United States Patent
Lee et al.

(10) Patent No.: US 12,173,342 B2
(45) Date of Patent: Dec. 24, 2024

(54) METHOD FOR PRODUCING MONOPHOSPHORYL LIPID A

(71) Applicants: EUBIOLOGICS CO., LTD., Seoul (KR); KOREA INSTITUTE OF SCIENCE AND TECHNOLOGY, Seoul (KR)

(72) Inventors: Chan Kyu Lee, Chuncheon-si (KR); Da Hui Ha, Chuncheon-si (KR); Choon Geun Lee, Chuncheon-si (KR); Ye Ram Lee, Chuncheon-si (KR); Hak Suk Chung, Seoul (KR)

(73) Assignees: EUBIOLOGICS CO., LTD., Seoul (KR); KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 130 days.

(21) Appl. No.: 17/630,657

(22) PCT Filed: Aug. 26, 2020

(86) PCT No.: PCT/KR2020/011425
§ 371 (c)(1),
(2) Date: Jan. 27, 2022

(87) PCT Pub. No.: WO2021/040414
PCT Pub. Date: Mar. 4, 2021

(65) Prior Publication Data
US 2022/0259633 A1    Aug. 18, 2022

(30) Foreign Application Priority Data

Aug. 29, 2019  (KR) .......... 10-2019-0106640
Aug. 25, 2020  (KR) .......... 10-2020-0107412

(51) Int. Cl.
*C12P 19/44* (2006.01)

(52) U.S. Cl.
CPC .................. *C12P 19/44* (2013.01)

(58) Field of Classification Search
CPC .................................................. C12P 19/44
See application file for complete search history.

(56) References Cited

U.S. PATENT DOCUMENTS

| 9,512,159 | B2 | 12/2016 | Myers et al. |
| 2007/0212758 | A1* | 9/2007 | Myers ............ A61P 37/04 435/85 |
| 2017/0191071 | A1* | 7/2017 | Chung ............ C12N 9/1029 |
| 2017/0198003 | A1* | 7/2017 | Xiao ............ C12Y 203/01085 |
| 2019/0010528 | A1 | 1/2019 | Chung et al. |

FOREIGN PATENT DOCUMENTS

| KR | 10-2008-0088666 A | 10/2008 |
| KR | 10-0884462 B1 | 2/2009 |
| KR | 10-2016-0028870 A | 3/2016 |
| KR | 10-1761348 B1 | 7/2017 |
| KR | 10-2019-0004966 A | 1/2019 |

OTHER PUBLICATIONS

Qureshi, Nilofer, et al. "Complete structural determination of lipopolysaccharide obtained from deep rough mutant of *Escherichia coli*. Purification by high performance liquid chromatography and direct analysis by plasma desorption mass spectrometry." Journal of Biological Chemistry 263.24 (1988): (Year: 1988).*
Pieretti, Giuseppina, et al. "A combined fermentative-chemical approach for the scalable production of pure *E. coli* monophosphoryl lipid A." Applied microbiology and biotechnology 98 (2014): 7781-7791. (Year: 2014).*
Myers, Kent R., et al. "Preparation and characterization of biologically active 6'-O-(6-aminocaproyl)-4'-O-monophosphoryl lipid A and its conjugated derivative." Bioconjugate chemistry 3.6 (1992): 540-548. (Year: 1992).*
International Search Report, issued in PCT/KR2020/011425, PCT/ISA/210, dated Nov. 30, 2020.
Qureshi et al., "Purification and Structural Determination of Nontoxic Lipid A Obtained from the Lipopolysaccharide of *Salmonella typhimurium*", The Journal of Biological Chemistry, Oct. 10, 1982, vol. 257, No. 19, pp. 11808-11815.
Wang et al., "Immuno-Stimulatory Activity of *Escherichia coli* Mutants Producing Kdo2-Monophosphoryl-Lipid A or Kdo2-Pentaacyl-Monophosphoryl-Lipid A", PLOS One, Dec. 28, 2015, total 16 pages.
Written Opinion of the International Searching Authority, issued in PCT/KR2020/011425, PCT/ISA/237, dated Nov. 30, 2020.

* cited by examiner

*Primary Examiner* — Robert J Yamasaki
*Assistant Examiner* — Trevor Kane
(74) *Attorney, Agent, or Firm* — Birch, Stewart, Kolasch & Birch, LLP

(57) ABSTRACT

Provided is a method of producing monophosphoryl lipid A (MPLA). According to the method, MPLA may be produced with high purity and high purity by using a bacterium producing MPLA.

14 Claims, 17 Drawing Sheets

Specification includes a Sequence Listing.

METHOD FOR PRODUCING MONOPHOSPHORYL LIPID A

CROSS REFERENCE TO RELATED APPLICATIONS

This application is the National Phase of PCT/KR2020/011425 filed on Aug. 26, 2020, which claims priority under 35 U.S.C. § 119 (a) to Patent Application Nos. 10-2019-0106640 and 10-2020-0107412 filed in the Republic of Korea on Aug. 29, 2019 and Aug. 25, 2020, respectively, all of which are hereby expressly incorporated by reference into the present application.

TECHNICAL FIELD

The present disclosure relates to a method of producing monophosphoryl lipid A (MPLA) with high purity and high efficiency by using a bacterium producing MPLA.

BACKGROUND ART

Lipopolysaccharide (LPS) is one of components of the outer membrane surrounding peptidoglycan of Gram-negative bacteria. LPS is a combination of lipid A and a variety of saccharides conjugated with the lipid A by a covalent bond, and is an endotoxin held responsible for the toxicity of Gram-negative bacteria. LPS stimulates toll-like receptor 4 (TLR4) of an immunocyte and drives critical immune responses. However, due to strong toxicity, only lipid A is isolated from LPS to be used as an immune booster.

Lipid A consists of two glucosamine backbones to which phosphate groups are bound at positions 1 and 4', and four acyl chains directly attached to the glucosamine head group at positions 2, 3, 2', and 3'. Two additional acyl chains are attached to hydroxyl groups of the acyl chains attached to the glucosamine head group at positions 2' and 3'. In a mechanism by which LPS acts as an endotoxin, the phosphate group bound at position 1 of the glucosamine backbone plays an important role. Monophosphoryl lipid A (MPLA, also referred to as 1-dephospho-lipid A) is a lipid in which the phosphate group at position 1 of the glucosamine head group in the structure of lipid A is substituted with a hydroxyl group. Unlike lipid A which has severe side effects, MPLA has excellent immune booster efficacy without having any side effects.

Recently, the development of a bacterium producing hexa-acylated MPLA and a method for producing the hexa-acylated MPLA using the bacterium has been disclosed (see KR 10-1761348 published on Jul. 19, 2017).

However, since lipid A and MPLA are contained together in the outer membrane of a bacterium and are structurally similar to each other, there is a need to develop a method of producing MPLA with high purity and high efficiency by separating the two substances.

DESCRIPTION OF EMBODIMENTS

Technical Problem

The present disclosure provides a method of producing monophosphoryl lipid A with high purity and high efficiency.

Solution to Problem

An aspect of the present disclosure provides a method of producing monophosphoryl lipid A (MPLA), the method including: culturing a bacterium producing MPLA, in which the bacterium is cultured from a starting point of an exponential phase to up to 5 hours after a starting point of a stationary phase in a growth curve; collecting the bacterium from the culture; obtaining lipid from the collected bacterium; and isolating MPLA from the obtained lipid.

In MPLA, lipid A consists of two glucosamines (carbohydrates or sugars) with acyl chains attached thereto, and generally each glucosamine includes one phosphate group. Depending on the number of the acyl chain, lipid A may be tri-, tetra-, penta-, hexa-, or hepta-acylated lipid A. Four acyl chains directly attached to glucosamine residues are beta hydroxy acyl chains consisting of 10 carbons to 16 carbons in length, and two additional acyl chains are usually attached to the beta hydroxy groups.

MPLA refers to a monophosphoryl lipid A in which one phosphate group is bound to only one of the two glucosamines. The MPLA may be tri-, tetra-, penta-, hexa,or hepta-acylated MLPA. For example, the MPLA may be 1-dephospho-lipid A, 1-dephospho-penta-acyl lipid A, 1-dephospho-tetra-acyl lipid A, or a combination thereof.

The MPLA may not include a sugar moiety. The sugar moiety may be 2-keto-3-deoxy-D-manno-octulosonate (Kdo). Kdo is a component of lipopolysaccharide (LPS), and is a conserved residue found in almost all LPS.

The MPLA may be present in a membrane, for example, in an outer membrane, of a living bacterium.

The method disclosed herein may include culturing a bacterium producing the MPLA.

The term "bacterium" as used herein refers to a prokaryotic bacterium. The bacterium may be a Gram-negative bacterium. A Gram-negative bacterium refers to a type of bacteria that do not stain with crystal violet used in a Gram staining method. The cell membrane of Gram-negative bacteria consists of a double membrane including an outer membrane and an inner membrane, and includes a thin peptidoglycan layer. The bacterium may be a bacterium selected from the group consisting of *Escherichia* genus bacteria, *Shigella* genus bacteria, *Salmonella* genus bacteria, *Campylobacter* genus bacteria, *Neisseria* genus bacteria, *Haemophilus* genus bacteria, *Aeromonas* genus bacteria, *Francisella* genus bacteria, *Yersinia* genus bacteria, *Klebsiella* genus bacteria, *Bordetella* genus bacteria, *Legionella* genus bacteria, Corynebacteria genus bacteria, *Citrobacter* genus bacteria, *Chlamydia* genus bacteria, *Brucella* genus bacteria, *Pseudomonas* genus bacteria, *Helicobacter* genus bacteria, *Burkholderia* genus bacteria, *Porphyromonas* genus bacteria, *Rhizobium* genus bacteria, *Mesorhizobium* genus bacteria, and *Vibrio* genus bacteria. For example, the bacterium may be *Escherichia coli* (*E. coli*).

The bacterium according to an embodiment may produce MPLA regardless of the presence of an expression inducer (for example, isopropyl β-D-1-thiogalactopyranoside (IPTG)) or an expression inducing stimulus (for example, heat treatment).

The bacterium according to an embodiment may include a lipid A-1 phosphatase (LpxE) polypeptide, a lipid A biosysthesis lauroyltransferase (LpxL) polypeptide, a lipid A biosysthesis myristoyltransferase (LpxM) polypeptide, or a combination thereof.

The LpxE polypeptide may include a tripartite active site, which consists of three amino acids, and six transmembrane helices, and may belong to the family of lipid phosphate phosphatases. A lipid phosphate phosphatase is a hydrolase, specifically binding to phosphoric monoester bonds, which may remove a phosphate group from a lipid containing a phosphate group. The LpxE polypeptide may be an LpxE polypeptide of a bacterium selected from the group consisting of *Helicobacter* genus bacterium (for example, *Helicobacter pylori*), *Aquifex* genus bacterium, *Francisella* genus bacterium, *Bordetella* genus bacterium, *Brucella* genus bacterium, *Rhizobium* genus bacterium, *Mesorhizobium* genus bacterium, and *Porphyromonas* genus bacterium. The LpxE polypeptide may be a polypeptide that includes an amino acid sequence of SEQ ID NO: 12, or a polypeptide having a sequence identity of about 90%, about 80%, about 70%, about 60%, about 50%, about 40%, about 30%, about 20%, or about 10% to the amino acid sequence of SEQ ID NO: 12. The LpxE polypeptide may be encoded by a polynucleotide that includes a nucleic acid sequence of SEQ ID NO: 13 or a nucleic acid having a sequence identity of about 90%, 80, about 70%, about 60%, about 50%, about 40%, about 30%, about 20%, about or about 10% to the nucleic acid of SEQ ID NO: 13. The LpxE polypeptide may be a mutated nucleotide sequence. For example, the polynucleotide may include a mutation of a nucleotide sequence that encodes the 17th amino acid serine (17Ser) from the N-terminal of a wild-type LpxE polypeptide, from AGC to TCG.

The LpxL polypeptide is a lipid A biosynthesis lauroyltransferase, which catalysts the transfer of laurate from a lauroyl-acyl carrier protein (ACP) to Kdo2-lipid IVA to synthesize a Kdo2-(lauroyl)-lipid IVA. The LpxL polypeptide may be an LpxL polypeptide of a bacterium selected from the group consisting of *Escherichia* genus bacteria, *Shigella* genus bacteria, *Salmonella* genus bacteria, *Campylobacter* genus bacteria, *Neisseria* genus bacteria, *Haemophilus* genus bacterium, an *Aeromonas* genus bacteria, *Francisella* genus bacteria, *Yersinia* genus bacteria, *Klebsiella* genus bacteria, *Bordetella* genus bacteria, *Legionella* genus bacteria, *Corynebacterium* genus bacteria, *Citrobacter* genus bacteria, *Chlamydia* genus bacteria, *Brucella* genus bacteria, *Pseudomonas* genus bacteria, *Helicobacter* genus bacteria, *Burkholderia* genus bacteria, *Porphyromonas* genus bacteria, *Rhizobium* genus bacteria, *Mesorhizobium* genus bacterium, and *Vibrio* genus bacteria. For example, the LpxL polypeptide may be an *E. coli* LpxL polypeptide (EcLpxL). The LpxL polypeptide may be a polypeptide that includes an amino acid sequence of SEQ ID NO: 1, or a polypeptide that has a sequence identity of about 90%, about 80%, about 70%, about 60%, about 50%, about 40%, about 30%, about 20%, or about 10% to the amino acid sequence of SEQ ID NO: 1. The LpxL polypeptide may be encoded by a nucleic acid sequence of SEQ ID NO: 2 or by a polynucleotide having a sequence identity of about 90%, 80, about 70%, about 60%, about 50%, about 40%, about 30%, about 20%, about or about 10% to the nucleic acid of SEQ ID NO: 2.

The LpxM polypeptide is a lipid A biosynthesis myristoyltransferase, which catalyzes the transfer of myristate from a myristoyl-acyl carrier protein to Kdo2-lauroyl-lipid IVA to synthesize Kdo2-lipid A. The LpxM polypeptide may be an LpxM polypeptide of a bacterium selected from the group consisting of *Escherichia* genus bacteria, *Shigella* genus bacteria, *Salmonella* genus bacteria, *Campylobacter* genus bacteria, *Neisseria* genus bacteria, *Haemophilus* genus bacteria, *Aeromonas* genus bacteria, *Francisella* genus bacteria, *Yersinia* genus bacteria, *Klebsiella* genus bacteria, *Bordetella* genus bacteria, *Legionella* genus bacteria, *Corynebacterium* genus bacteria, *Citrobacter* genus bacteria, *Chlamydia* genus bacteria, *Brucella* genus bacteria, *Pseudomonas* genus bacteria, *Helicobacter* genus bacteria, *Burkholderia* genus bacteria, *Porphyromonas* genus bacteria, *Rhizobium* genus bacteria, *Mesorhizobium* genus bacteria, and *Vibrio* genus bacteria. For example, the LpxM polypeptide may be an *E. coli* LpxM polypeptide (EcLpxM). The LpxM polypeptide may be a polypeptide that includes an amino acid sequence of SEQ ID NO: 5, or a polypeptide that has a sequence identity of about 90%, about 80%, about 70%, about 60%, about 50%, about 40%, about 30%, about 20%, or about 10% to the amino acid sequence of SEQ ID NO: 5. The LpxM polypeptide may be encoded by a nucleic acid sequence of SEQ ID NO: 6 or by a polynucleotide having a sequence identity of about 90%, 80, about 70%, about 60%, about 50%, about 40%, about 30%, about 20%, about or about 10% to the nucleic acid of SEQ ID NO: 6.

The bacterium may include a mutation in a polynucleotide encoding a LpxT polypeptide, a polynucleotide encoding a PagP polypeptide, a polynucleotide encoding a KdtA polypeptide, or a combination thereof. The LpxT polypeptide may be an inner membrane protein LpxT. The PagP polypeptide is a lipid A palmitoyltransferase, which is required for biosynthesis of a hepta-acyl lipid A species including palmitate. The KdtA polypeptide may be an enzyme that binds Kdo to lipid IVA. The term "mutation" as used herein refers to a mutation of genetic material, and may include a point mutation, a frameshift mutation, an insertion, a deletion, an inversion, a translocation, or the like. By a mutation, a genetic material may be deleted from or introduced into the genome of the bacterium.

The bacterium may include, in a bacterial chromosome thereof, a mutation in a polynucleotide encoding an undecaprenyl pyrophosphate phosphatase (Und-PP phosphatase), a polynucleotide encoding a phosphatidylglycerophosphate phosphatase (PGP phosphatase), or a combination thereof. The term "bacterial chromosome" as used herein contains genetic information of the bacterium, and may be circular DNA. The bacterial chromosome may be plasmid-free. A plasmid refers to circular DNA that is physically separated from a bacterial chromosome and is able to replicate independently.

The Und-PP phosphatase is an enzyme that produces an undecaprenyl phosphate by catalyzing dephosphorylation of an undecaprenyl pyrophosphate. An undecaprenyl phosphate is a lipid carrier of a glycan biosynthetic intermediate for a hydrocarbon polymer that is delivered to the envelope of a bacterium. The polynucleotide encoding the Und-PP phosphatase may be a bacA gene, a pgpB gene, a ybjG gene, or a combination thereof. The bacA gene is a gene that confers resistance to an antibiotic material, bacitracin, at the time of overexpression. The pgpB gene is a gene encoding an enzyme that catalyzes dephosphorylation of phosphatidylglycerol phosphate (PGP) to generate phosphatidyl glycerol (PG), and may have Und-PP phosphatase activity. The ybjG gene is a gene that enhances the Und-PP phosphatase activity and increases resistance to bacitracin, at the time of overexpression.

The polynucleotide encoding the PGP phosphatase may be a pgpB gene, a pgpA gene, a pgpC gene, or a combination thereof. The pgpA gene or pgpC gene is a gene encoding a lipid phosphatase that dephosphorylates PGP to PG.

The term "gene" as used herein is a unit of genetic information, and may include an open reading frame (ORF) that encodes a polypeptide and a regulatory sequence that regulate gene transcription. The regulatory sequence may include a promoter which is a DNA domain where gene transcription is initiated, an enhancer that promote transcription, a silencer that inhibits transcription, or a combination thereof.

The term "mutation" as used herein refers to a mutation in a genetic material, and may include a point mutation, a frameshift mutation, an insertion, a deletion, an inversion, a translocation, or the like. For example, the mutation may be a deletion, an insertion, a point mutation, a frameshift mutation, or a combination thereof. The point mutation may be a missense mutation or a nonsense mutation. By a mutation, a genetic material may be deleted from or introduced into the genome of the bacterium.

A type of culture medium, a culturing temperature, and culturing conditions may be the same as those known in the art. A culture medium may include an antibiotic. The antibiotic may be, for example, kanamycin, ampicillin, chloramphenicol, or a combination thereof.

The bacterium may be cultured from a starting point of an exponential phase until up to about 5 hours after a starting point of a stationary phase in a growth curve. The growth curve of a bacterium may be divided into a lag phase, an exponential phase or a log phase, a stationary phase, and a death phase. The lag phase refers to a period in which a bacterium is adapted to growth conditions and is not yet able to divide. The exponential phase refers to a period in which a bacterium divide exponentially, unless growth is restricted. The stationary phase refers to a period initiated by depletion of important nutrients or formation of inhibitory products such as organic acids, and also refers to a period in which a rate of bacterial death and a rate of bacterial proliferation are the same. The death phase refers to a period in which the rate of bacterial proliferation decreases due to the depletion of nutrients or the like. The bacterium may be cultured from a starting point of the exponential phase to a starting point of the stationary phase, or may be cultured for about 1 hour, about 1.5 hours, about 2 hours, about 2.5 hours, about 3 hours, about 3.5 hours, about 4 hours, about 4.5 hours, about less than 5 hours, or up to about 5 hours after a starting point of the stationary phase from a starting point of the exponential phase.

The bacterium may be cultured with optical density (OD, or absorbance) in a range of about in a range at an 10 to about 70, about 15 to about 70, about 20 to about 70, about 25 to about 70, about 30 to about 70, about 35 to about 70, about 40 to about 70, about 45 to about 70, about 50 to about 70, about 55 to about 70, about 50 to about 68, about 50 to about 66, about 50 to about 64, about 50 to about 62, about 50 to about 61, or about 55 to about 62, at a wavelength of 600 nm.

The bacterium may be cultured for about 10 hours to about 30 hours, about 12 hours to about 30 hours, about 14 hours to about 30 hours, about 16 hours to about 30 hours, about 18 hours to about 30 hours, about 20 hours to about 30 hours, about 21 hours to about 30 hours, about 21 hours to about 29 hours, about 21 hours to about 28 hours, about 21 hours to about 27 hours, about 21 hours to about 26 hours, about 21 hours to about 25 hours, about 21 hours to about 24 hours, about 21 hours to about 23 hours, or about 21 hours to about 22 hours.

The bacterium may be cultured at a temperature in a range of about 25° C. to about 40° C., about 26° C. to about 40° C., about 27° C. to about 40° C., about 28° C. to about 40° C., about 29° C. to about 40° C., about 30° C. to about 40° C., about 31° C. to about 40° C., about 32° C. to about 40° C., about 33° C. to about 40° C., about 34° C. to about 40° C., about 35° C. to about 40° C., about 36° C. to about 40° C., about 37° C. to about 40° C., about 30° C. to about 39° C., about 30° C. to about 38° C., about 30° C. to about 37° C., about 30° C. to about 36° C., about 30° C. to about 35° C., about 30° C. to about 34° C., about 30° C. to about 33° C., about 30° C. to about 32° C., or about 30° C. to about 31° C.

A culture method of the bacterium may be the same as known in the art. The culture method may be, for example, batch culture, fed-batch culture, continuous culture, fermentation, or a combination thereof. The bacterium may be cultured while shaking.

The method disclosed herein may include collecting the bacterium from the culture.

The collecting of the bacterium from the culture may be known in the art. For example, the collecting of the bacterium may be performed by centrifugation, filtration, or a combination thereof. The collected bacterium may be washed with a buffer.

The method disclosed herein may include obtaining a lipid from the collected bacterium. The obtaining of the lipid may be known in the art. The PMLA may be obtained by using a physical or chemical method. The physical method may, for example, repeatedly use ultrasound pulses or freezing-thawing. The chemical method may include an extraction process using an organic solvent. The organic solvent may be, for example, chloroform, phenol, petroleum ether, dichloromethane, methanol, hexane, isopropyl alcohol, ethyl acetate, acetonitrile, ethanol, butanol, or a combination thereof. The obtaining of the lipid may be, for example, performed by a Bligh and Dyer extraction protocol (see Bligh, E. G. and Dyer, W. J., Can. J. Biochem. Physiol., 1959, vol. 37, p.911-917).

The method disclosed herein may include isolating MPLA from the obtained lipid.

The method disclosed herein may not include removing a sugar moiety from the obtained lipid. Here, the sugar moiety may be Kdo.

The isolating of MPLA may be performed by chromatography. The chromatography is separation of a mixture according to affinity between an adsorbent (for example, a stationary phase or a resin) and a sample, and is a method in which a sample is eluted by flowing a solvent (for example, a mobile phase or a buffer). The chromatography may be ion-exchange chromatography, thin-layer chromatography (TLC), liquid chromatography (LC), reversed-phase chromatography, or a combination thereof.

The ion-exchange chromatography may be a method of separating ions or polar molecules by using electrostatic interaction with anions or cations bound to a stationary phase (or a resin). The ion-exchange chromatography may be anion-exchange chromatography or cation-exchange chromatography. A resin used in the ion-exchange chromatography may be, for example, cellulose, sephadex, or sepharose. A resin used in the anion-exchange chromatography may be a diethylaminoethyl (DEAE) group, a diethyl-2-hydroxypropylaminoethyl group or a quaternary aminoethyl (QAE) group, or a quaternary ammonium (Q) functional group. For example, the resin used in the anion-exchange chromatography may be DEAE cellulose, QAE sephadex, Q ammonium, or a combination thereof. For example, the resin used in the anion-exchange chromatography may be MACRO-PREP HIGH Q-3HT®, UNO SPHERE Q®, NUVIA Q® resin, and DE52® resin.

A buffer used in the ion-exchange chromatography may include ammonium acetate, ammonium formate, pyridinium formate, pyridinium acetate, ammonium carbonate, or a combination thereof. An eluent used in the ion-exchange chromatography may include chloroform, methanol, water, or a combination thereof.

The TLC refers to chromatography in which a material is developed and separated by using a particulate carrier as a stationary phase and a solvent as a mobile phase, wherein the particulate carrier is uniformly applied on a support such as a glass plate or an aluminum foil.

The LC refers to chromatography using liquid as a mobile phase. The LC chromatography may be high-performance liquid chromatography (HPLC).

The reversed-phase chromatography refers to chromatography in which a mixture is separated by using a combination of a stationary phase having a low polarity and a mobile phase having a high polarity. In the reversed-phase chromatography, a material in which a hydrocarbon chain, a phenyl group, a cyano group, an amine group, or a combination thereof is conjugated to silica gel may be used as a stationary phase. Here, the hydrocarbon chain may be a $C_8$ chain, a $C_4$ chain, or a $C_{18}$ chain.

A buffer used in the reversed-phase chromatography may include chloroform, methanol, acetonitrile, phosphoric acid, ammonium acetate, water, or a combination thereof.

In the reversed-phase chromatography, elution is performed by a step concentration gradient or a linear concentration gradient.

ADVANTAGEOUS EFFECTS OF DISCLOSURE

Monophosphoryl lipid A (MPLA) may be produced with high purity and high efficiency from a bacterium producing MPLA.

MODE OF DISCLOSURE

Hereinafter, the present disclosure will be described in more detail with reference to Examples below. However, these Examples are for illustrative purposes only, and the scope of the present disclosure is not intended to be limited by these Examples.

Example 1. Preparation of Strain Producing MPLA 1.1. Preparation of vector including polynucleotide that encodes lipidases, *E. coli* LpxL and *E. coli* LpxM
1.1.1. Preparation of pWSK29-EcLpxLEcLpxM To obtain a polynucleotide encoding an *E. coli* LpxL polypeptide, from the *E. coli* W3110 genome (GenBank Accession No. NC_000918.1, ATCC), a polynucleotide (GenBank Accession No. AP009048.1 (c1118159.1117239, SEQ ID NO: 2), which encodes an EcLpxL polypeptide (GenBank Accession No. BAA35852.1, SEQ ID NO: 1) including a ribosome binding site (RBS), was amplified by first polymerase chain reaction (PCR) using a pair of primers below:

```
LpxL forward primer P1:
                                    (SEQ ID NO: 3)
5'-CGCAGTCTAGAAAGGAGATATATTGATGACGAATTACCCAAGT

TCTC-3'

LpxL reverse primer P2:
                                    (SEQ ID NO: 4)
5'-CGCTATTATTTTTTTTCGTTTCCATTGGTATATCTCCTTCTTA

TTAATAGCGTGAAGGAACGCCTTC-3'.
```

Figure 1A:
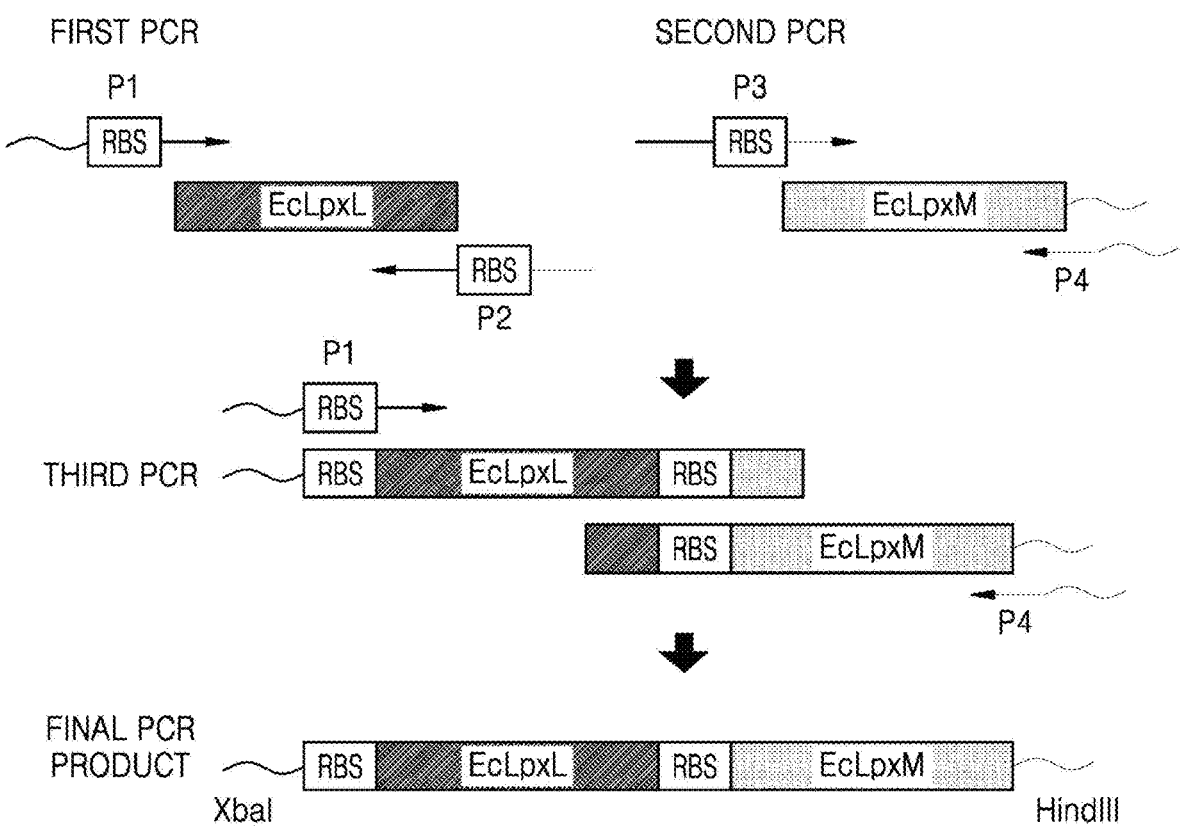
FIG. 1A is a schematic view illustrating a process of producing a PCR product including EcLpxL and EcLpxM.

To obtain a polynucleotide encoding an *E. coli* LpxM polypeptide, from the *E. coli* W3110 genome, a polynucleotide (GenBank Accession No. AP009048.1 (c1941907.1940936, SEQ ID NO: 6), which encodes an EcLpxM polypeptide (GenBank Accession No. BAA15663.1, SEQ ID NO: 5) including an RBS, was amplified by second PCR using a pair of primers below (see FIG. 1A):

```
LpxM forward primer P3:
                                    (SEQ ID NO: 7)
5'-GAAGGCGTTCCTTCACGCTATTAATAAGAAGGAGATATACCAA

TGGAAACGAAAAAAAATAATAGCG-3'

LpxM reverse primer P4:
                                    (SEQ ID NO: 8)
5'-GCAGAAGCTTTTATTTGATGGGATAAAGATCTTTGCG-3'.
```

Then, an EcLpxLEcLpxM polynucleotide in which the EcLpxL polynucleotide of the first PCR and the EcLpxM polynucleotide of the second PCR were fused was amplified by third PCR using, as templates, the EcLpxL polynucleotide and the EcLpxM polynucleotide, and as primers, the LpxL forward primer P1 and the LpxM reverse primer P4.

The PCRs were each performed by using a KOD HOT START DNA POLYMERASE® (Novagen) in a T3000 THERMOCYCLER® (Biometra).

The amplified products were purified by using a DOKDO-PREP PCR® purification kit (ELPIS-BIOTECH. Inc.), and the purified products were introduced into a pWSK29 plasmid (see Wang, R. F., and Kushner, S. R., Gene (1991), vol. 100, p. 195-199). Such a cloned plasmid was transformed into *E. coli* DH5a by electroporation, and the transformed *E. coli* was then selected on an LB-ampicillin plate. The cloned plasmid was named pWSK29-EcLpxLEcLpxM (see FIG. 1A).

1.1.2. Preparation of pKHSC0004

To modify a promoter sequence of the pWSK29-EcLpxLEcLpxM into a $P_L$ promoter sequence (5'-TTGACATAAATACCACTGGCGGTGATACT-3': SEQ ID NO: 9), site-directed mutagenesis was performed by PCR using the pWSK29-EcLpxLEcLpxM prepared in Section 1.1.1 as a template and a pair of primers below:

```
Forward primer amplifying P_L promoter:
                                  (SEQ ID NO: 10)
5'-GGCAGTGAGCGCAACGCAGAATTCTTGACATAAA

TACCACTGGCGGTGATACTTTCACACAGGAAACAGCTATGACC-3'

Reverse primer amplifying P_L promote:
                                  (SEQ ID NO: 11)
5'-GGTCATAGCTGTTTCCTGTGTGAAAGTATCACCG

CCAGTGGTATTTATGTCAAGAATTCTGCGTTGCGCTCACTGCC-3'.
```

The PCR was performed by using A QUIKCHANGE SITE-DIRECTED MUTAGENESIS KIT® (Agilent) in a T3000 THERMOCYCLER® (Biometra).

After the site-directed mutagenesis, the reaction product was treated with a Dpn1 restriction enzyme (ELPIS-BIOTECH. Inc.).], and then transformed into *E. coli* DH5a by electroporation. The transformed *E. coli* was selected on an LB-ampicillin plate. The cloned plasmid was named pKHSC0004.

1.2. Preparation of pBAD30-HpLpxE-Frt-Kan-Frt Encoding Phosphatase 1.2.1. Preparation of pBAD30-HpLpxE To delete a HindIII restriction enzyme recognition site sequence, a hp0021 gene encoding *Helicobacter pylori* LpxE (HpLpxE) had a mutation of a nucleotide sequence that encodes the 17th amino acid serine (17Ser) from the N-terminal, from AGC to TCG. The mutated hp0021 gene was synthesized by INTEGRATED DNA® technologies (mBiotech, Republic of Korea).

A polynucleotide (SEQ ID NO: 13) encoding an HpLpxE amino acid sequence (SEQ ID NO: 12) was amplified by PCR using the mutated hp0021 gene as a template and a pair of primers below:

```
Forward primer for amplifying HpLpxE mutant:
                                  (SEQ ID NO: 14)
5'-GATCCTCTAGAAAGGAGATATATTGATGAAAAAATTCTTATTTAAA

CAAAAATTT-3'

Reverse primer for amplifying HpLpxE mutant:
                                  (SEQ ID NO: 15)
5'-AGCTACAAGCTTTTAAGGCTTTTTGGGGC-3'.
```

The PCR was performed by using a KOD HOT START DNA POLYMERASE® (Novagen) in a T3000 THERMOCYCLER® (Biometra).

As described in Section 1.1.1, the PCR was performed, and the amplified products thus obtained were purified. The purified products were cloned into a pBAD30 plasmid (see Guzman, L. M., Belin, D., Carson, M. J., Beckwith, J., J Bacteriol (1995). 177 (14), p.4121-4130). Such a cloned plasmid was transformed into *E. coli*, and the transformed *E. coli* was then selected as described above in Section 1.1.1. The cloned plasmid was named pBAD30-HpLpxE.

1.2.2. Preparation of pBAD30-HpLpxE-frt-kan-frt

A frt-kan-frt polynucleotide having HindIII restriction enzyme recognition site sequences at both terminals was amplified by PCR using a pair of primers below and a pKD4 plasmid (Kirill A. Datsenko, and Barry L. Wanner PNAS (2000), vol. 97, p.6640-6645) as a template:

```
Forward primer for amplifying frt-kan-frt:
                                  (SEQ ID NO: 16)
5'-GCAGAAGCTTGTGTAGGCTGGAGCTGCTTC-3'

Reverse primer for amplifying frt-kan-frt:
                                  (SEQ ID NO: 17)
5'-GCAGAAGCTTATGAATATCCTCCTTAGTTCCTAT-3'.
```

The PCR was performed by using a pfu DNA polymerase (ELPIS-BIOTECH. Inc.) in a T3000 THERMOCYCLER® (Biometra). As described in Section 1.1.1, the PCR was performed, and the amplified products thus obtained were purified.

The purified products were cloned into the pBAD30-HpLpxE plasmid obtained in Section 1.2.1. The cloned plasmid was transformed into *E. coli*, and the transformed *E. coli* was then selected from as described in Section 1.1.1. The cloned plasmid was named pBAD30-HpLpxE-frt-kan-frt.

1.3. Preparation of *E. coli* Strain 1.3.1. Preparation of *E. coli* in which lpx T Gene was Removed from Genome An *E. coli* strain, i.e., IpxT::kan, W3110, in which a kanamycin cassette was inserted into an IpxT gene (SEQ ID NO: 19) in the *E. coli* genome was prepared, the IpxT gene encoding an LpxT polypeptide (SEQ ID NO: 18).

Then, a pCP20 plasmid (Kirill A. Datsenko, and Barry L. Wanner PNAS (2000), vol. 97, p.6640-6645) was transformed into the IpxT::kan, W3110. The transformed *E. coli* was selected and inoculated on an LB solid medium, and selected at 42° C., so as to prepare an *E. coli* strain, i.e., ΔIpxT, W3110, from which the IpxT gene and the kanamycin cassette were removed.

1.3.2. Preparation of *E. coli* in which pagP and IpxT Genes were Removed from Genome P1 virus was prepared from an *E. coli* strain (JW0617 (pagP::kan), (Keio *E. coli* knockout library) in which a kanamycin cassette was inserted into a pagP gene in the *E. coli* genome. The P1 virus was transduced into the ΔIpxT, W3110 prepared in Section 1.3.1. The transduced *E. coli* was then selected on an LB-kanamycin solid medium, so as to prepare an *E. coli* strain, i.e., ΔIpxT, pagP::kan, W3110, to which pagP::kan was inserted instead of the pagP gene.

The same pCP20 plasmid as described in Section 1.3.1 was transformed into the ΔIpxT, pagP::kan, W3110, and the transformed *E. coli* was then selected on a LB-ampicillin solid medium. The selected *E. coli* was inoculated on an LB solid medium and selected at 42° C., so as to prepare an *E. coli* strain, i.e., ΔIpxT, ΔpagP, W3110, from which the pagP gene and the kanamycin cassette were removed.

1.3.3. Preparation of *E. coli* in which IpxT and pagP Genes were Removed from Genome and bacA Gene was Replaced by HpLpxE-Frt-Kan-Frt Polynucleotide To prepare a bacA::HpLpxE-frt-kan-frt polynucleotide which enables homologous recombination with the bacA gene, amplification was performed by PCR using the pBAD30-HpLpxE-frt-kan-frt prepared in Section 1.2.2 as a template and a pair of primers below:

```
Forward primer for amplifying bacA::HpLpxE-frt-
kan-frt:
                                    (SEQ ID NO: 20)
5'-AACCTGGTCATACGCAGTAGTTCGGACAAGCGGTACATTTTAATAA

TTTAGGGGTTTATTGATGAAAAAATTCTTATTTAAACAAAAAT-3'

Reverse primer for amplifying bacA::HpLpxE-frt-
kan-frt:
                                    (SEQ ID NO: 21)
5'-TGACAACGCCAAGCATCCGACACTATTCCTCAATTAAAAGAACACG

ACATACACCGCAGCCGCCACATGAATATCCTCCTTAGTTCCTA-3'.
```

The PCR was performed by using a pfu DNA polymerase (ELPIS) in a T3000 THERMOCYCLER® (Biometra).

Figure 1B:
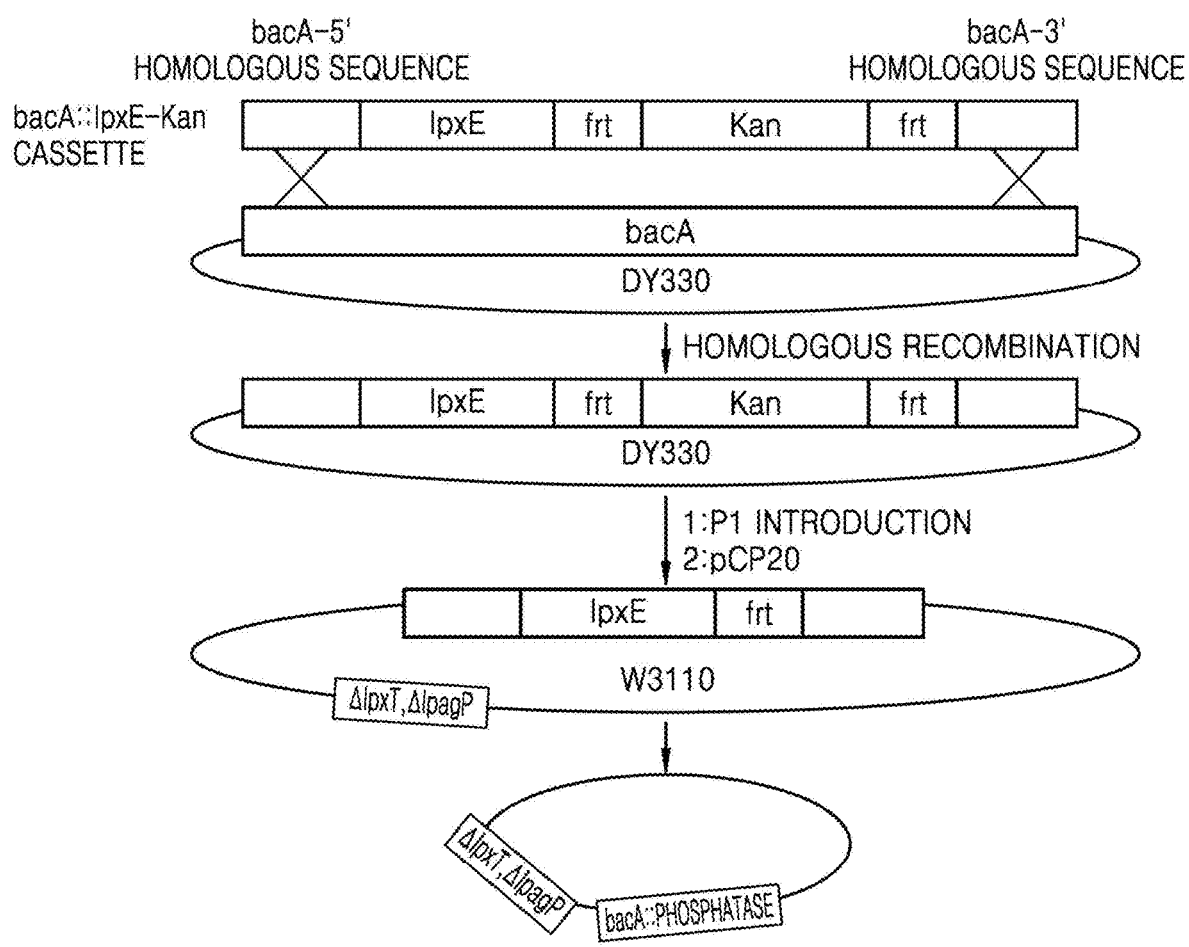
FIG. 1B is a schematic view illustrating a method of replacing a bacA gene of an *Escherichia coli* chromosome with an IpxE gene encoding a phosphatase, by using a homologous recombination method.

As described in Section 1.1.1, the PCR was performed, and the amplified products thus obtained were purified. The purified products were transformed into *E. coli* DY330 (Yu, D., et. al., PNAS. (2000). 97 (11), p5978-5983) by electroporation. By the transformation, an *E. coli* bacA::HpLpxE-frt-kan-frt, DY330 strain was prepared through homologous recombination with upstream and downstream sequences of the bacA gene in the DY330 genome (see FIG. 1B).

P1 virus was prepared from the bacA::HpLpxE-frt-kan-frt, DY330 strain. The P1 virus was transduced into the *E. coli* strain, i.e., ΔlpxT, ΔpagP, W3110, prepared in Section 1.3.2, and the transduced *E. coli* was then selected on an LB-kanamycin solid medium. The selected *E. coli* was named ΔlpxT, ΔpagP, bacA::HpLpxE-frt-kan-frt, W3110 (see FIG. 1B).

Figure 1C:
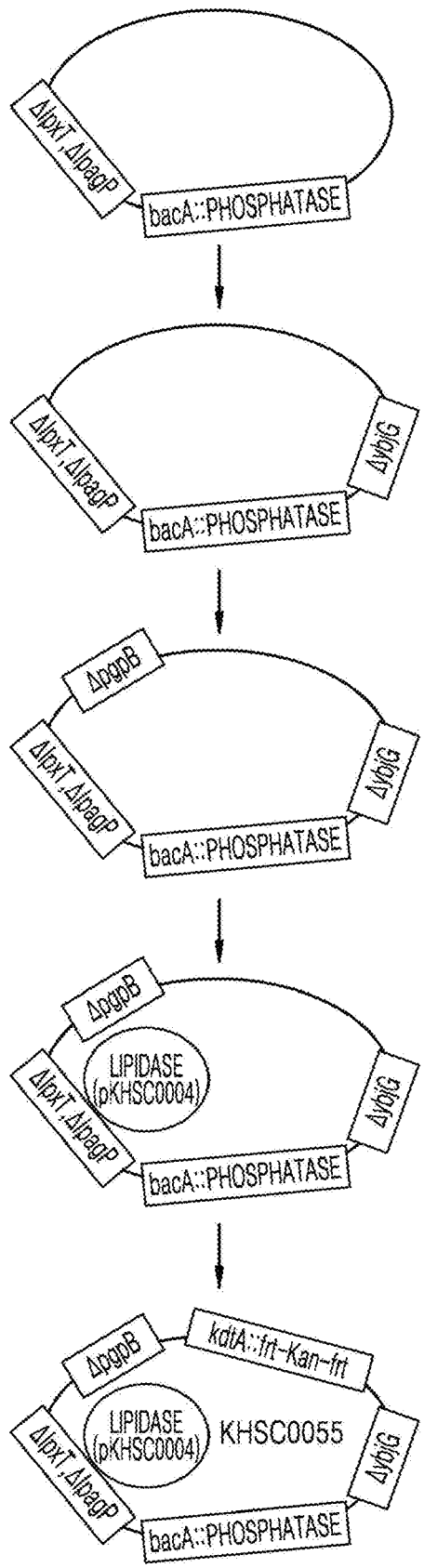
FIG. 1C is a schematic view illustrating a process of constructing a strain in which activity of a phosphotase inserted into the chromosome is stabilized.

1.3.4. Preparation of *E. coli* in which lpx T and pagP Genes were Removed from Genome and bacA Gene was Replaced by HpLpxE Gene The same pCP20 plasmid as described in Section 1.3.1 was transformed into the ΔlpxT, ΔpagP, bacA::HpLpxE-frt-kan-frt, W3110 as described in Section 1.3.3, and the transformed *E. coli* was then selected on an LB-ampicillin solid medium. The selected *E. coli* were inoculated on an LB solid medium and selected at 42° C., so as to prepare an *E. coli* strain, i.e., ΔlpxT, ΔpagP, bacA::HpLpxE, W3110, from which bacA and the kanamycin cassette were removed and into which HpLpxE was introduced (see the first row of FIG. 1C).

1.3.5. Preparation of *E. coli* in which lpxT, pagP, and ybjG Genes were Removed from Genome and bacA Gene was Replaced by HpLpxE Gene P1 virus was prepared from an *E. coli* JW5112(ybjG::kan) strain (Keio *E. coli* knockout library) in which a kanamycin cassette was inserted into a ybjG gene in the *E. coli* genome. The P1 virus was transduced into the ΔlpxT, ΔpagP, bacA::HpLpxE, W3110 prepared in Section 1.3.4. The transduced *E. coli* was then selected on an LB-kanamycin solid medium, so as to prepare an *E. coli* strain, i.e., ΔlpxT, ΔpagP, bacA::HpLpxE, ybjG::kan, W3110, to which ybjG::kan was inserted instead of the ybjG gene.

The same pCP20 plasmid as described in Section 1.3.1 was transformed into the ΔlpxT, ΔpagP, bacA::HpLpxE, ybjG::kan, W3110, and the transformed *E. coli* was then selected on an LB-ampicillin solid. The selected *E. coli* were inoculated on an LB-ampicillin solid medium and selected at 42° C., so as to prepare an *E. coli* strain, i.e., ΔlpxT, ΔpagP, ΔybjG, bacA::HpLpxE, W3110, from which the ybjG gene and the kanamycin cassette were removed (see the second row of FIG. 1C).

1.3.6. Preparation of *E. coli* pKHSC0004 Strain (ΔlpxT, ΔpagP, ΔybjG, ΔpgpB, bacA::HpLpxE, W3110)

P1 virus was prepared from an *E. coli* strain (JW1270 (pgpB::kan), Keio *E. coli* knockout library) in which a kanamycin cassette was inserted into a pgpB gene in the *E. coli* genome. The P1 virus was transduced into the ΔlpxT, ΔpagP, ΔybjG, bacA::HpLpxE, W3110 prepared in Section 1.3.6, and the transduced *E. coli* was then selected on an LB-kanamycin solid medium, so as to prepare an *E. coli* strain, i.e., ΔlpxT, ΔpagP, ΔybjG, bacA::HpLpxE, pgpB::kan W3110, to which pgpB::kan was inserted instead of the pgpB gene.

The same pCP20 plasmid as described in Section 1.3.1 was transformed into the ΔlpxT, ΔpagP, ΔybjG, bacA::HpLpxE, pgpB::kan, W3110, and the transformed *E. coli* was then selected on an LB-ampicillin solid. The selected *E. coli* were inoculated on an LB solid medium and selected at 42° C., so as to prepare an *E. coli* strain, i.e., ΔlpxT, ΔpagP, ΔybjG, ΔpgpB, bacA::HpLpxE, W3110, from which pgpB and the kanamycin cassette were removed (see the third row of FIG. 1C).

The pKHSC0004 plasmid prepared in Section 1.1.2 was transformed into the *E. coli* strain, i.e., ΔlpxT, ΔpagP, ΔybjG, ΔpgpB, bacA::HpLpxE, W3110, by electroporation. The transformed *E. coli* was selected on an LB-ampicillin solid medium, so as to prepare an *E. coli* pKHSC0004 strain, i.e., ΔlpxT, ΔpagP, ΔybjG, ΔpgpB, bacA::HpLpxE, W3110 (see the fourth row of FIG. 1C).

1.3.7. Preparation of *E. coli* KHSC0055 Strain

*E. coli* including a pEcKdtA plasmid and a kanamycin cassette (frt-kan-frt) inserted into a kdtA gene (SEQ ID NO: 23) in the *E. coli* chromosome was prepared as follows, the kdtA gene encoding a KdtA polypeptide (SEQ ID NO: 22).

To amplify a kdtA::frt-kan-frt polynucleotide which enables homologous recombination with the kdtA gene, amplification was performed by PCR using a pKD4 plasmid (Kirill A. Datsenko, and Barry L. Wanner PNAS (2000), vol. 97, p.6640-6645) as a template and a pair of primers below:

```
Forward primer for amplifying kdtA::frt-kan-frt:
                                    (SEQ ID NO: 24)
5'-GCTAAATACATAGAATCCCCAGCACATCCATAAGTCAGCTATTTAC

TATGCTCGAATTGCGTGTAGGCTGGAGCTGCTTC-3'

Reverse primer for amplifying kdtA::frt-kan-frt:
                                    (SEQ ID NO: 25)
5'-ATCGATATGACCATTGGTAATGGGATCGAAAGTACCCGGATAAATC

GCCCGTTTTTGCATTGAATATCCTCCTTAGTTCCTATTCC-3'.
```

The PCR was performed by using a pfu DNA polymerase (ELPIS) in a T3000 THERMOCYCLER® (Biometra).

As described in Section 1.1.1, the PCR was performed, and the amplified products thus obtained were purified. The purified products were transformed into *E. coli* DY330 including a pEcKdtA plasmid (Chung, H. S., and Raetz, C. R., Biochemistry (2010), vol. 49 (19), p.4126-4137) by electroporation. By the transformation, an *E. coli* pEcKdtA, kdtA::frt-kan-frt, DY330 strain was prepared through homologous recombination with upstream and downstream sequences of the kdtA gene in the DY330 genome (see FIG. 1B). P1 virus was prepared from the pEcKdtA, kdtA::frt-kan-frt, DY330 strain. The P1 virus was transduced into the *E. coli* pKHSC0004 strain, i.e., ΔlpxT, ΔpagP, ΔybjG, ΔpgpB, bacA::HpLpxE, W3110, prepared in Section 1.3.6, and the transduced *E. coli* was then selected on an LB-kanamycin solid medium. The selected *E. coli* was named KHSC0055 (pKHSC0004, ΔlpxT, ΔpagP, ΔybjG, ΔpgpB, bacA::HpLpxE, kdtA::frt-kan-frt, W3110) (see the fifth row of FIG. 1C).

1.4. Confirmation of Lipid Compositions of *E. coli* KHSC0055 Strain 1.4.1. Culture of KHSC0055 Strain The *E. coli* KHSC0055 strain was prepared as described in Section 1.3.7. A KHSC0055 stock was inoculated into 3 mL of an LB broth medium containing 50 μg/mL of ampicillin, and then cultured overnight at 30° C. The resulting culture medium was inoculated into 200 mL of a fresh LB broth medium containing 50 μg/mL of ampicillin, and then cultured overnight at 30° C.

1.4.2. Lipid Extraction from *E. coli* KHSC0055 Strain

The *E. coli* culture medium cultured as described in Section 1.4.1 was centrifuged at room temperature at a speed of 4,000×g for about 20 minutes to obtain *E. coli* from each strain. The obtained *E. coli* was washed with 30 mL of PBS, and then resuspended in 8 mL of PBS.

10 mL of chloroform and 20 mL of methanol were added to the resuspended *E. coli*, and then cultured at room temperature for about 1 hour with occasional shaking. Then, the cultured mixture was centrifuged at room temperature at a speed of 2,500×g for about 30 minutes to collect a supernatant. 10 mL of chloroform and 10 ml of water were added to the collected supernatant, mixed completely, and then centrifugated at room temperature at 2,500×g for about 20 minutes. After an organic solvent layer was isolated from the centrifuged mixture, the organic solvent layer was extracted twice by adding a pre-equilibrated organic solvent layer to the upper aqueous layer. The organic solvent layer was pooled, and then dried in a rotary evaporator to obtain lipids. The obtained lipids were dissolved in 5 mL of a 4:1(v/v) mixture of chloroform and methanol, and then subjected to ultrasonic irradiation in a water bath. The ultrasonically irradiated lipids were moved to a new test tube, and the obtained lipids were dried at room temperature in a nitrogen gas environment and then stored at about −80° C.

1.4.3. TLC Analysis for Lipid

Membrane lipids of *E. coli* of each strain isolated as described above in Section 1.4.2 were analyzed. Here, MPLA SYNTHETIC® (InvivoGen, Catalog Code: tlrl-mpls, synthetic 1-diphosphoryl-hexaacylated lipid A (see Lane 1 of FIG. 1D) was used as a positive control group.

Figure 1D:
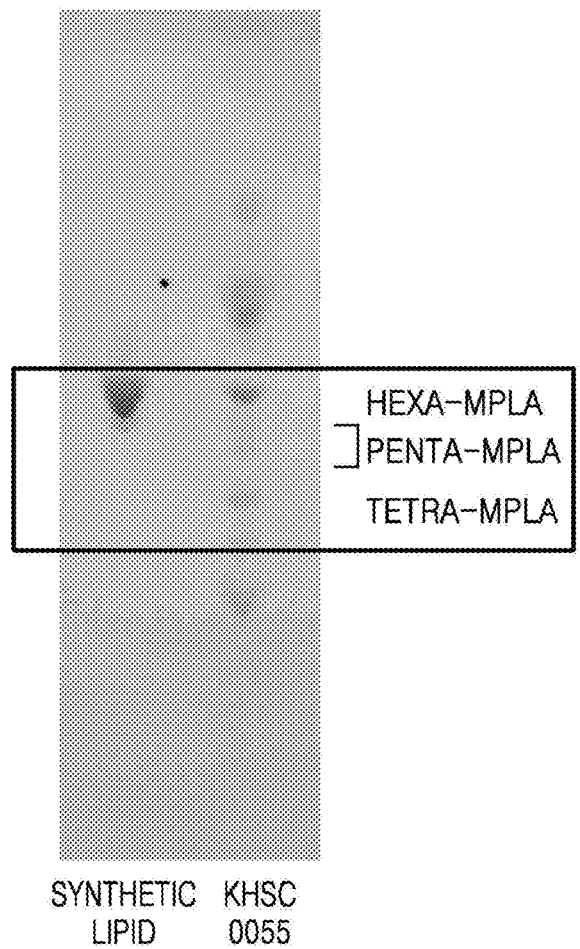
FIG. 1D is an image showing TLC results for lipid obtained from a KHSC0055 strain.

To perform TLC, lipid was obtained from 200 mL of the *E. coli* culture medium as described in Section 1.4.2, and one-third of the total lipids thus obtained was dissolved in 200 μl of a 4:1 (v/v) mixture of chloroform:methanol. Afterwards, about 5 μl to about 15 μl of the mixture was spotted on a 10×10 cm HPTLC PLATE® (EMD Chemicals) and developed in a solvent mixture of chloroform:methanol:water:ammonium hydroxide (28% (v/v) ammonia) in a ratio of 40:25:4:2 (v/v). The developed plate was dried, visualized by spraying with 10% (v/v) of sulfuric acid (in ethanol), and then heated on a hot plate of 300° C. The TLC results of the liquids are shown in FIG. 1D. In FIG. 1D, Lane 1 represents the synthetic 1-dephospho-hexa-acylated lipid A (InvivoGen, Catalog code: tlrl-mpls), and Lane 2 represents lipid isolated from KHSC0055 stain.

As shown in FIG. 1D, it was confirmed that the *E. coli* strain KHSC0055 was living *E. coli* effectively producing 1-dephospho-hexa-acylated lipid A. Therefore, the strain KHSC0055 was a genetically engineered strain in which the core-polysaccharide and O-antigen of LPS were removed without affecting the survival of cells and in which lipid A and MPLA from which one phosphate group was removed from lipid A were directly accumulated and produced in the outer membrane of the cell.

Example 2. Production of MPLA with High Purity and High Efficiency 2.1. Culture of Strain Producing MPLA 2.1.1. Preparation of Medium The culture of the strain prepared in Section 1.4.3 was performed in a 30 L fermenter, and a seed culture medium and a main culture medium were prepared separately. Here, as the seed culture medium, 16.0 g/L of peptone (BD Biosciences), 10 g/L of yeast extract, and 5 g/L of NaCl were used after being sterilized, and 100 μg/mL of ampicillin was added right before the strain culture. As the main culture medium, 3.5 g/L of peptone (BD Biosciences), 21.0 g/L of yeast extract, 6.0 g/L of $KH_2PO_4$, 5.0 g/L of $K_2HPO_4$, and 5.0 g/L of $NH_4Cl$ were used after being sterilized, and 40.0 g/L of glucose and 10.0 g/L of $MgSO_4 \cdot 7H_2O$ were also sterilized to aseptically add to the main incubator while culturing the strain.

2.1.2. Seed Culture

For primary seed culture, 200 ml of a sterilized seed culture medium was added to a 1 L Erlenmeyer flask. A seed vial of the strain KHSC0055 was thawed, added to the flask, and incubated in a shaker incubator at about 31° C. for about 18 hours to about 22 hours.

For secondary seed culture, 600 mL of a sterilized seed culture medium was added to each of six Erlenmeyer flasks (2 L), and 35 mL of the primary seed culture solution was inoculated thereto. The cells were then cultured in a shaker incubator at about 31° C. for about 7 hours to about 12 hours.

2.1.3. Main Culture

Figure 2:
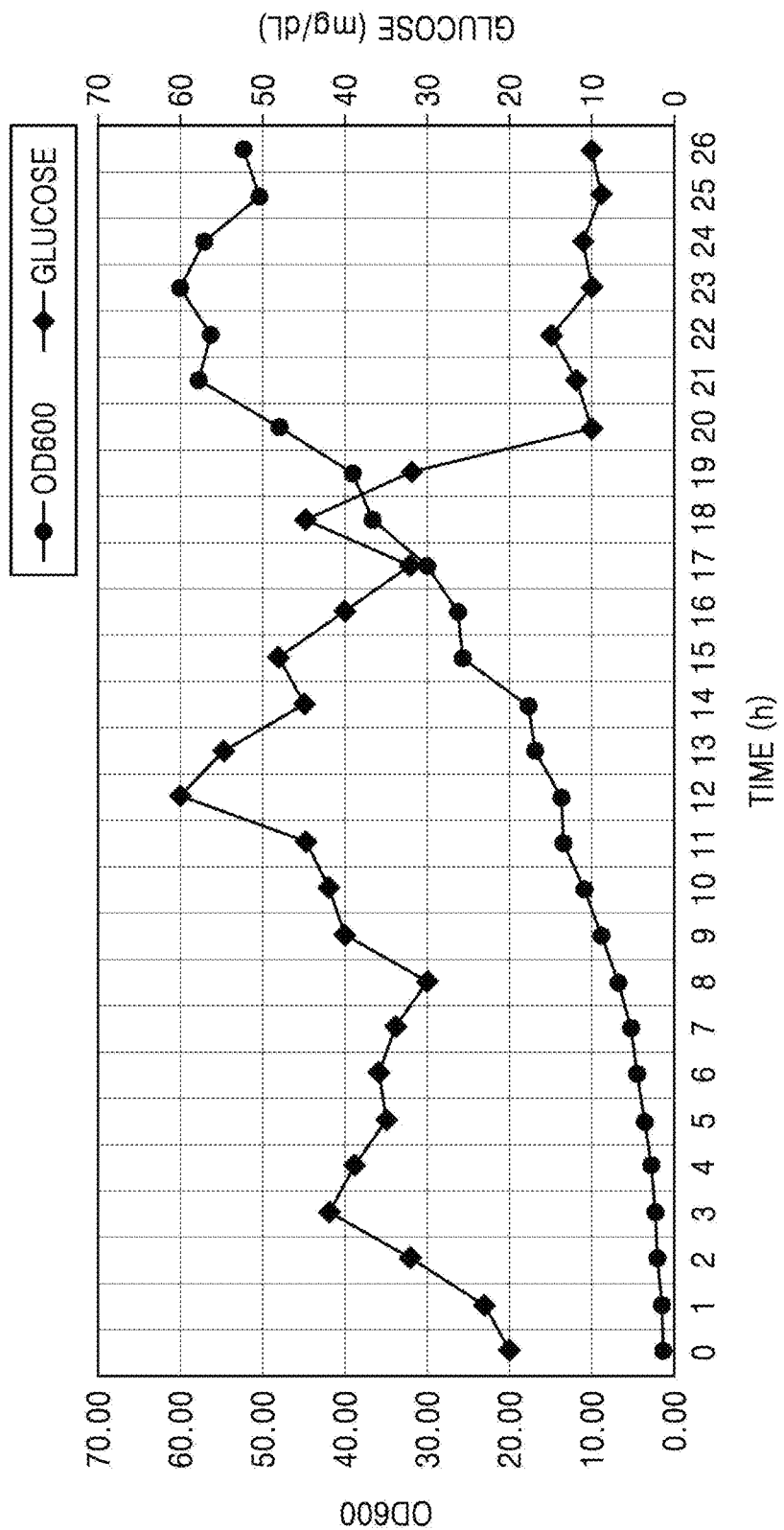
FIG. 2 is a graph showing a cell growth curve from a main culture of an *E. coli* KHSC0055 strain.

The main culture was performed in a 30 L fermenter with initial working volume of 18 L. The fermenter vessel was filled with 18 L of the main culture medium and sterilized. Then, a glucose solution which was sterilized separately was aseptically added to the incubator during incubation. Here, the concentration of glucose in the culture medium was adjusted to 1 g/L or less. The pH of the medium was maintained at pH 6.7 by using $NH_4OH$. After the secondary seed culture was inoculated into the fermenter, was inoculated with a secondary seed culture, the aeration was adjusted to 3.0 Lpm at about 31° C. and the dissolved oxygen (DO) was adjusted to about 50%. Then, the cells were cultured while stirring at a speed in a range of about 300 rpm to about 400 rpm. The growth stage of the culture was monitored by measuring the absorbance at 600 nm (see FIG. 2).

Regarding the recovery of the culture medium, the culture medium was collected when *E. coli* passed the exponential growth phase and reached the death phase after the stationary phase. The culture medium was filtered by one of centrifugation and tangential flow filtration, washed with PBS, and then frozen.

2.1.4. Lipid Extraction and TLC Analysis

The culture medium was centrifuged at room temperature for about 20 minutes to obtain *E. coli* only. 10 mL of the obtained *E. coli* was washed with 40 mL of PBS, and then centrifuged again to obtain *E. coli* only. After performing a washing process twice, the resultant was resuspended in 10 mL of PBS. To 5 ml of resuspended *E. coli,* 12.5 mL of methanol and 6.25 mL of chloroform were added, and the mixture was incubated at room temperature for 1 hour while shaking. The incubated mixture was centrifuged at room temperature for about 30 minutes to obtain a supernatant. To the obtained supernatant, 6.25 mL of each of methanol and chloroform was thoroughly mixed, followed by centrifugation at room temperature for 20 minutes. An organic solvent layer was separated from the centrifuged mixture, and dried in a nitrogen dryer to extract lipid A and 1-dephospho-lipid A. The obtained lipid was refrigerated.

Figure 3:
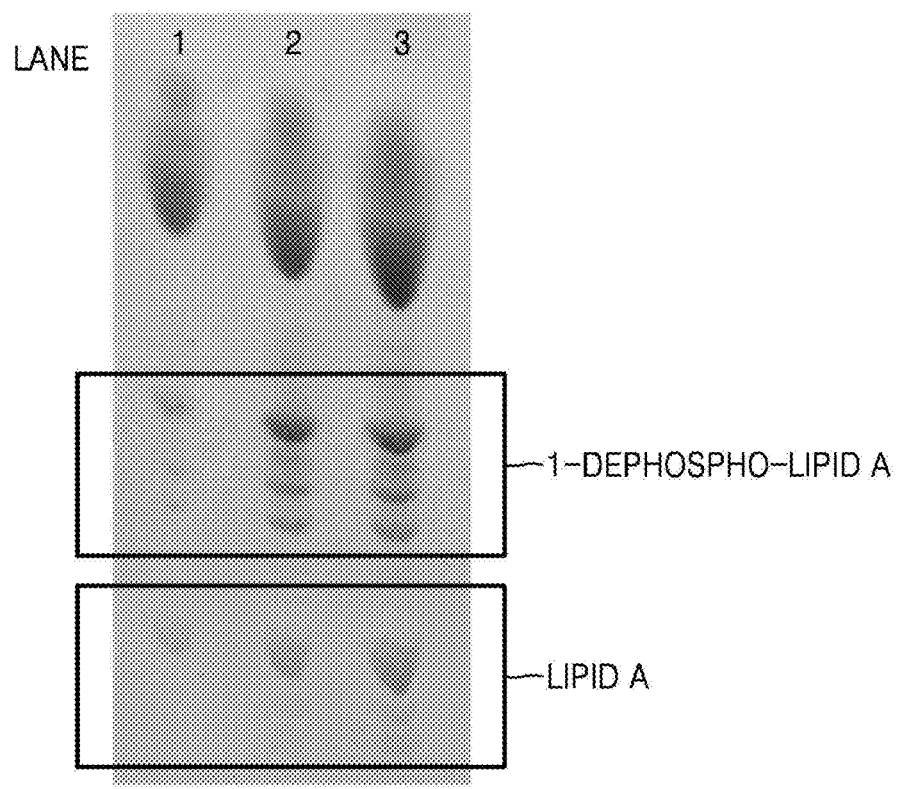
FIG. 3 is an image showing TLC analysis results for total lipids obtained from a culture medium of an *E. coli* KHSC0055 strain.

The TLC analysis was performed as described in Section 1.4.3, and the results are shown in FIG. 3. In FIG. 3, Lanes 1, 2, and 3 were loaded with 5 µl, 10 µl, and 15 µl of the obtained lipid at 1 mg/ml, respectively. As shown in FIG. 3, it was confirmed that the extracted lipid was a mixture of lipid A and 1-dephospho-lipid A.

2.1.5. Changes in Lipid Content and Composition According to Cell Growth

The way of changes in total lipid contents depending on the growth of E. coli was tested. The lipid was extracted as described in Section 2.1.4 by sampling 30 ml of the culture medium of 2.1.3 by hour. After the extraction, all solvents were dried through nitrogen drying, and then the weight was measured.

TABLE 1

| Culture time (h) | Absorbance (OD600) | Total lipid content (mg) |
|---|---|---|
| 12 | 13.8 | 4.5 |
| 14 | 17.9 | 5.5 |
| 16 | 26.1 | 8 |
| 18 | 36.7 | 11 |
| 20 | 48.0 | 12.6 |
| 21 | 58.0 | 13.5 |
| 22 | 56.4 | 14.8 |
| 23 | 60.2 | 14.6 |
| 24 | 57.2 | 15.6 |
| 25 | 50.6 | 14.7 |
| 26 | 52.4 | 14.6 |

Figure 4A:
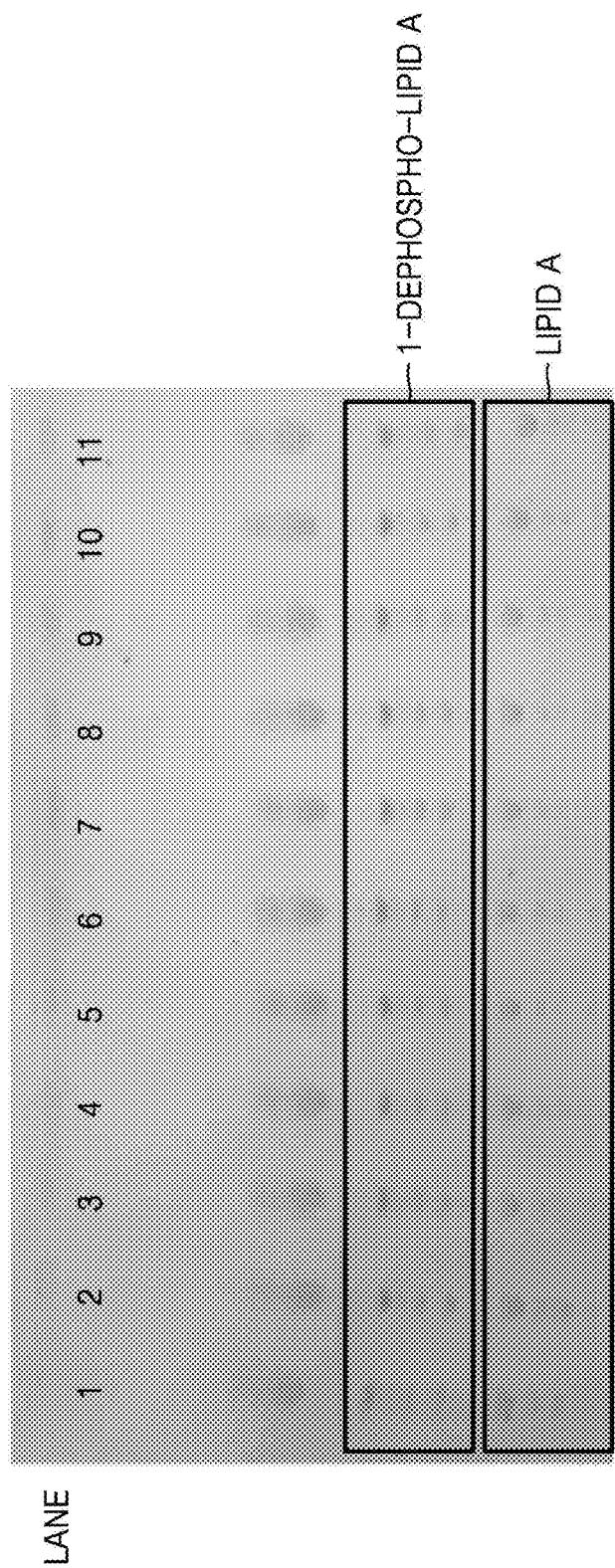
FIG. 4A is an image showing TLC analysis results for lipid A and 1-deacyl-lipid A according to culture time of *E. coli*.

As shown in Table 1, little change in the total lipid contents was observed after the cell growth of E. coli reached the stationary phase (after about 21 hours later) until the death phase. To confirm changes in the lipid composition depending on the growth of E. coli, 1 mg/ml of the extracted lipid was dissolved in a 2:1 (v/v) chloroform:methanol solution. The TLC analysis was performed as described in Section 1.4.3, and the results are shown in FIG. 4A. In FIG. 4A, Lanes 1 to 11 were loaded with lipids extracted from the culture medium after being cultured for 12, 14, 16, 18, 20, 21, 22, 23, 24, 25, and 26 hours, respectively. The ratio between 1-dephospho-lipid A to lipid A was measured by using CHEMIDOC® (BIO-RAD), and the results are shown in FIG. 4B.

Figure 4B:
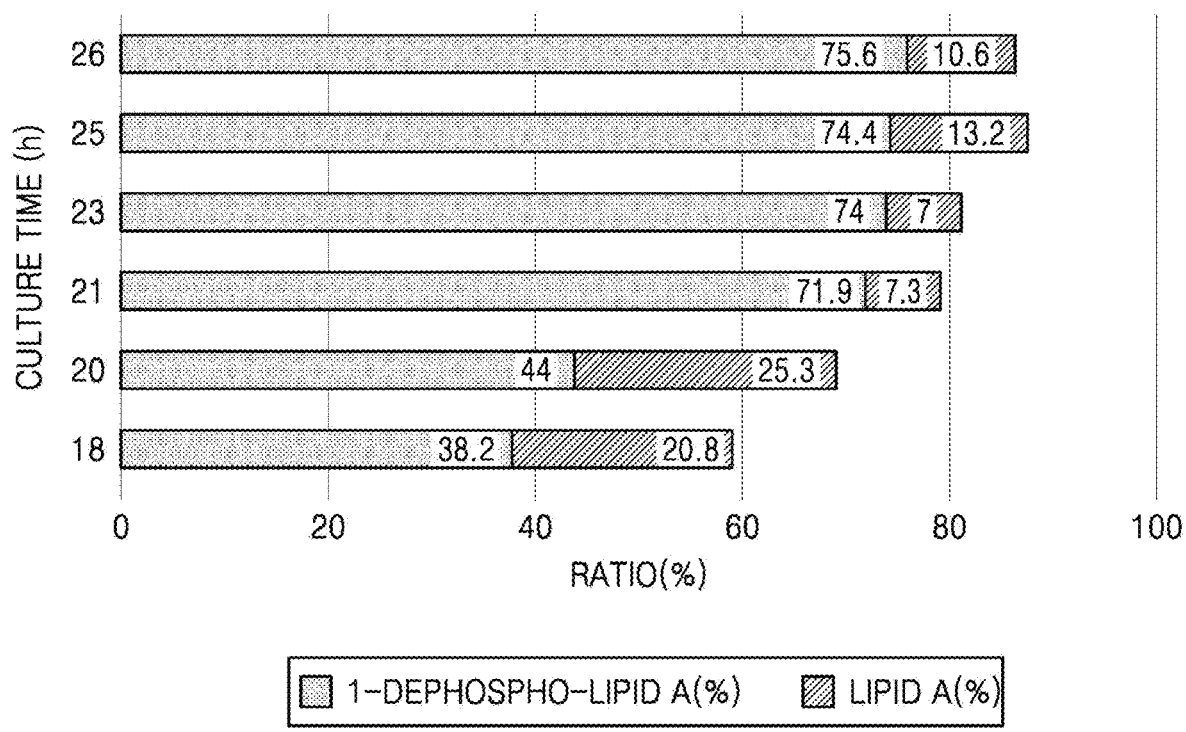
FIG. 4B is a graph showing ratios of 1-dephospho-lipid A and lipid A in lipids according to culture time of *E. coli*.

As shown in FIGS. 4A and 4B, there was no significant change in the ratio between lipid A and 1-dephospho-lipid A after the stationary phase of cell growth. Since the precursors of 1-dephospho-lipid A extracted from Salmonella had acylation pattern in LPS that changed according to the recovery time of the culture medium, the cells were known to be recovered after 5 hours to 6 hours in stationary phase in the cell growth (see claim 1 of KR 10-0884462 (published on Feb. 11, 2009)). However, it was confirmed in the present disclosure that the strain KHSC0055 showed little change in the deacyl pattern according to the recovery time after the stationary phase in the cell growth and that lipid A and 1-dephospho-lipid A were produced at a certain ratio as the culture time elapsed.

Therefore, it was confirmed that the recovery of the culture medium of the strain KHSC0055 facilitated the recovery of cells when the cell growth reached the stationary phase to apply the status of the cells and the next process, such as centrifugation or tangential flow filtration.

2.1.6. Purification of 1-Dephospho-Lipid A

To purify 1-dephospho-lipid A from the total lipids, ion-exchange chromatography was performed.

For ion-exchange chromatography, cellulose matrix-based IONSEP DEAE DE52 CELLULOSE PRESWOLLEN® (BiopHoretics Co.) and polymer matrix-based MACRO PREP DEAER (Bio-Rad Laboratories, Inc.) were used. MACRO PREP DEAER is a weak anion exchange resin, and includes —$HN^+(C_2H_5)$ 2 as a functional group. Since an organic solvent was used in the purification method, a material of the column may be glass or stainless steel.

To obtain only 1-dephosphoric acid-lipid A from the mixture of lipid A and 1-dephosphoric acid-lipid A, the purification was performed by a gradient of ammonium acetate. The resin was equilibrated by flowing a solution of chloroform:methanol:distilled water (2:3:1, v/v) with a column volume (CV) of 10 CV or more. 3 mg/ml of the lipid extract was loaded onto the equilibrated resin. By washing the resin with a solution of chloroform:methanol:distilled water (2:3:1, v/v) with 20 CV or more, the impurities derived from E. coli were sufficiently wiped off to allow elution.

For elution of 1-dephospho-lipid A, the elution was performed by a gradient of chloroform:methanol:5 mM to 50 mM of salt (ammonium acetate) (2:3:1, v/v). Here, the TLC analysis was performed for each fraction eluted by 1 CV (see FIG. 5A). As a result of the TLC analysis, the fractions eluted with 1-dephospho-lipid A only were collected and pooled in a separatory funnel. To improve buffer exchange and stability of 1-dephospho-lipid A, 10 ml of chloroform per 60 ml of the pooled solution was added, followed by addition of 0.1 N HCl solution. Here, the final ratio of chloroform:methanol:distilled water ratio was 2:2:1.8 (v/v). The separatory funnel was mixed well to mix all the solutions evenly, and was left until all the solutions are separated into two layer. Here, a phase change occurred from one phase in which the organic solvent layer including 1-dephospho-lipid A dissolved therein and the aqueous solution layer including lipid A dissolved therein to two phases in which the organic solvent layer and the aqueous solution layer were isolated from each other. By isolating the organic solvent layer only, 1-dephospho-lipid A was obtained. For elution of lipid a still attached to the resin, the resin was regenerated with a high concentration (500 mM to 1 M) of salt (ammonium acetate).

Figure 5A:
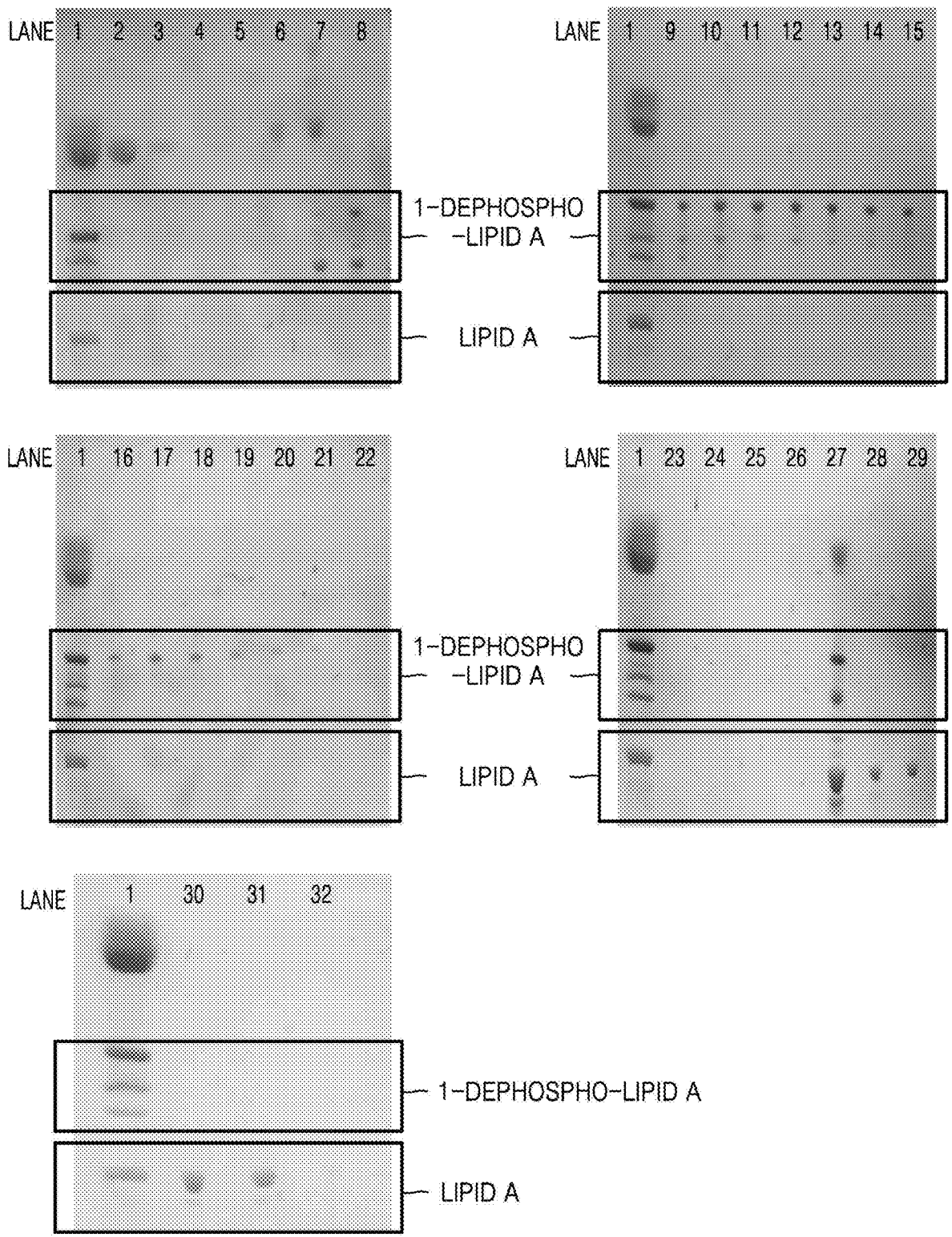
FIG. 5A is an image showing TLC analysis results for an eluate by a salt concentration gradient after total lipids are purified by ion-exchange chromatography.

The TLC analysis results for each eluate are shown in FIG. 5A (Lane 1: lipid sample before purification, Lanes 2 to 5: Washing after loading lipid samples; Lanes 6 to 25: Fractions by 1 CV by a salt gradient (1-dephospho-lipid A elution), Lanes 26 to 32: Washing with high-concentration salt (lipid A elution)). In addition, in the purification of 1-dephospho-lipid A, a comparison result between the case of using a DE52® resin and the case of using a MACRO PREP DEAER resin are shown in Table 5B.

Figure 5B:
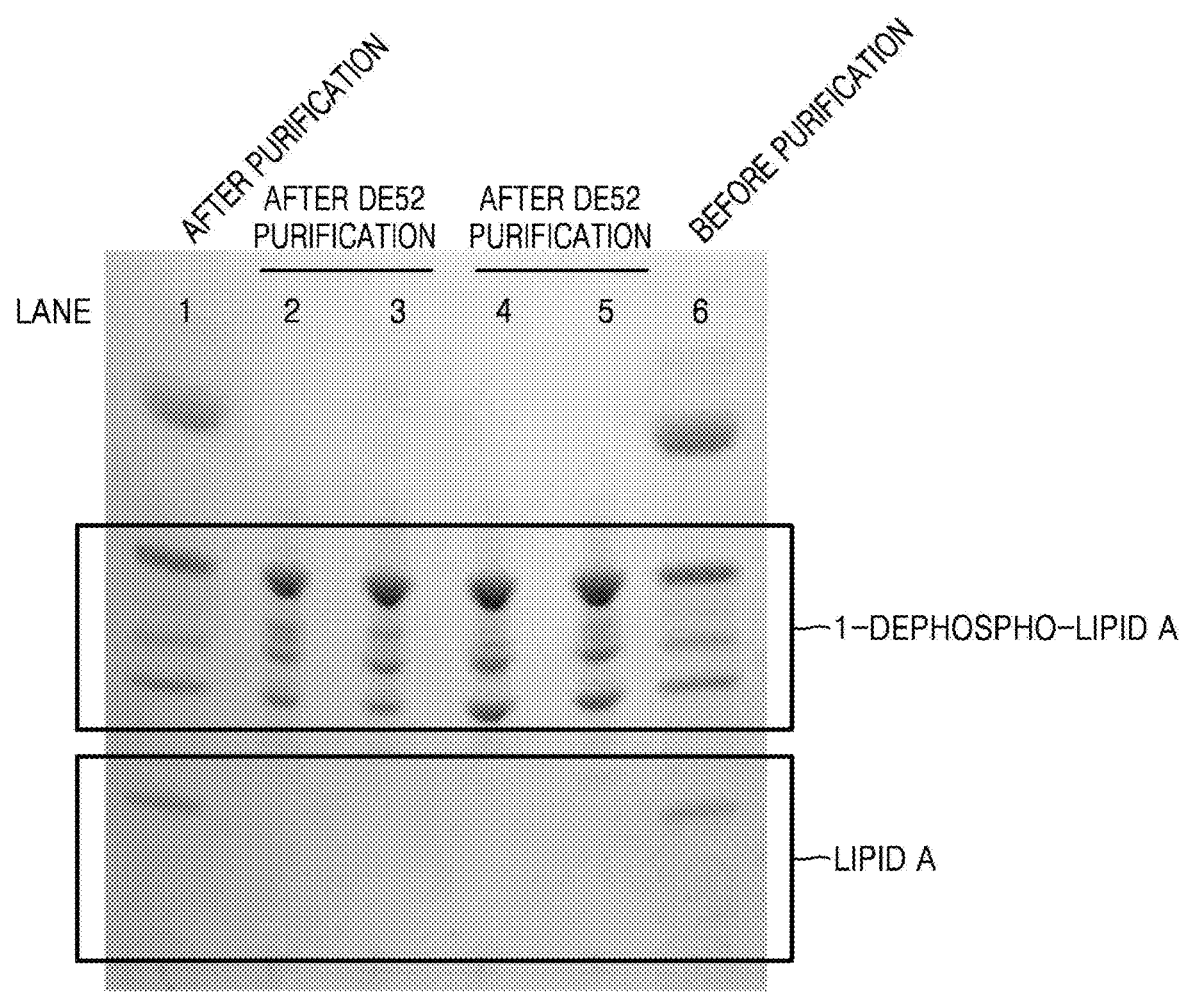
FIG. 5B is an image showing TLC analysis results for purified 1-dephospho-lipid A when purified by using a DE52® resin or a MACRO-PREP DEAE® resin.

As shown in FIGS. 5A and 5B, it was confirmed that 1-dephospho-lipid A may be purified with high purity by ion-exchange chromatography.

2.1.7. Resin Screening for Purification of 1-Dephospho-Lipid A

The purification was attempted with not only DE52® and MACRO PREP DEAE® resins, but also other polymer matrix-based anion-exchange resins such as MACRO-PREP HIGH Q-3HT®, UNO SPHERE Q®, AND NUVIA Q®.

Figure 6:
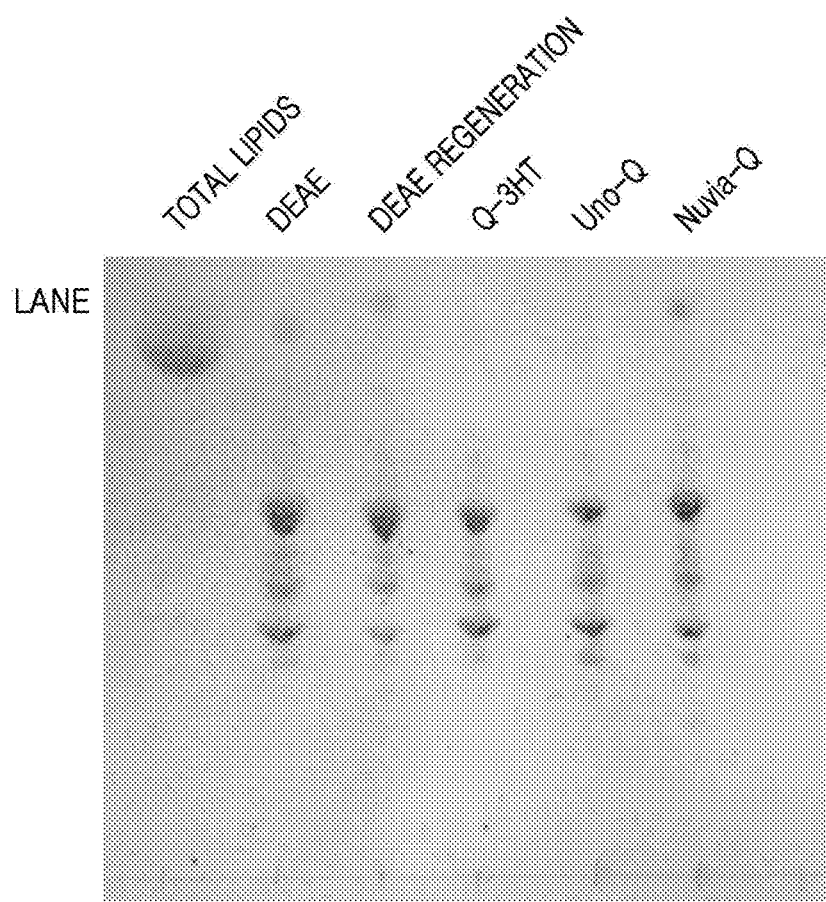
FIG. 6 is an image showing TLC analysis results for purified 1-dephospho-lipid A when purified by using various types of ion-exchange resin.

The results of purifying 1-dephospho-lipid A and TLC confirmation are shown in FIG. 6 (Lane 1: lipid sample before purification, Lane 2:1-dephospho lipid A purified by using macro-prep DEAE, Lane 3:1-dephospho-lipid A reused after purifying by using MACRO-PREP DEAE and regenerating, Lane 4:1-dephospho lipid A purified by using MACRO-PREP HIGH Q-3HT®, Lane 5:1-dephospho lipid A purified by using UNO SPHERE Q®, and Lane 6:1-dephospho lipid A purified by using NUVIA Q®).

As shown in FIG. 6, it was confirmed that 1-dephospho-lipid A was purified from the lipid extract. In addition, after 1-dephospho-lipid A was purified by using a macro-prep DEAE resin, the resin was regenerated by a high salt gradient. Since the resin regeneration was successfully achieved, it was confirmed that 1-dephospho-lipid A was purified from the mixture with lipid A even after the resin regeneration.

2.1.8. Measurement of Phosphate Group Content in Lipid a and 1-Dephospho-Lipid A Due to the difference in the number of phosphate groups, lipid A has two molecules of the phosphate group, whereas the 1-dephospho-lipid A has one molecule of the phosphate group. Thus, 1 M lipid A has 2 M phosphate groups, and the 1 M lipid as 1 M phosphate group.

The lipid obtained from the strain KHSC0055 may be a mixture of isomers due to the diversity of the number and position of fatty acids attached to the backbone of lipid A. To measure the phosphate group content in the obtained 1-dephospho-lipid A, the following method was used.

Figure 7:
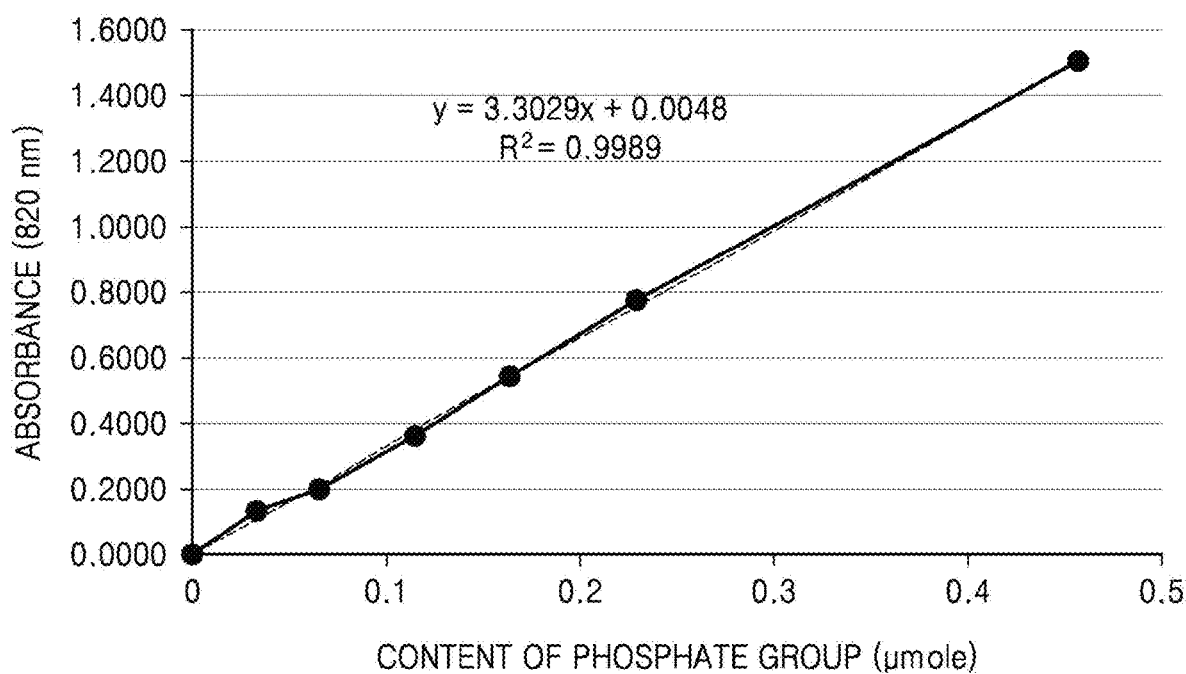
FIG. 7 is a standard curve showing phosphate group content in lipids.

A quantitative curve was prepared by using the standard 0.65 mM PHOSPHORUS STANDARD SOLUTION® (Sigma cat. no. P3869). 0 μmole of black, and 0.0325 μmole (50 μl), 0.065 μmole (100 μl), 0.114 μmole (175 μl), 0.163 μmole (250 μl), and 0.228 μmole (350 μl) of the standard solution were each added to a glass test tube. 0.45 mL of 8.9 N $H_2SO_4$ was added to each of the glass test tubes, and incubated at a temperature in a range of about 200° C. to about 215° C. for 25 minutes. After cooling the heated glass test tubes at room temperature for 5 minutes, 150 μl of $H_2O_2$ was added thereto, and incubated at a temperature in a range of about 200° C. to about 215° C. for 30 minutes. After cooling the heated glass test tubes at room temperature, 3.9 mL of distilled water was added thereto and sufficiently stirred. To each glass test tube, 0.5 mL of 2.5% (w/v) ammonium molybdate (VI) tetrahydrate solution was added and sufficiently stirred. To each glass test tube, 0.5 mL of 10% (w/v) ascorbic acid solution was added and sufficiently stirred. Then, to prevent vaporization of the liquid, each glass test tube was tightly closed with a lid and incubated at 100° C. for 7 minutes. The samples were cooled to room temperature, and transferred to a 96-well plate. By using an ELISA reader, the absorbance was measured at 820 nm, and the standard curve for the measured content of the phosphate group was shown in FIG. 7. Here, R2 value of the standard curve was 0.9989, which is reliable.

Referring to the standard curve for the content of the phosphate group, the contents of the phosphate groups in the total lipids before the purification and 1-dephospho-lipid A and lipid A after the purification were calculated. The calculated results are shown in Table 2.

TABLE 2

| Sample | Total lipids (before purification) | 1-dephospho-lipid A (after purification) | Lipid A (after purification) |
| --- | --- | --- | --- |
| Content of phosphate group (μmol/mg) | 0.91 | 0.55 | 1.09 |

As shown in Table 2, the phosphate group content of the total lipids before the purification was 0.91 μmol/mg, the phosphate group content of 1-dephospho-lipid A was 0.55 μmol/mg, and the phosphate group content of lipid A was 1.09 μmol/mg which is twice as the phosphate group content of 1-dephospho-lipid A. Thus, it shows that only 1-dephospho-lipid A was obtained from total lipids through the purification.

2.1.9. Purification of 1-Dephospho-Lipid a by Reversed-Phase Chromatography

After performing the purification of 1-dephospho-lipid A from lipid by ion-exchange chromatography, reverse-phase chromatography was performed for the separation purification of remaining phospholipids derived from *E. coli* and the control of the content of isoforms of 1-dephospho-lipid A.

As a resin for the separation and purification, a SMT BULK C8 RESIN® (Separation Methods Technologies, Inc.) was used. Purification conditions varied by the difference in the solvent polarity. Ammonium acetate was used to ionize the sample. As a buffer, 15:75:10 (v/v) of chloroform: methanol:distilled water (Buffer A) and 15:85 (v/v) chloroform:methanol (Buffer B) were used. In both buffers, 20 mM ammonium acetate was dissolved. Purification methods are as follows. The resin was equilibrated by flowing 10 CV or more of 100% Buffer A. A mixture (sample) of purified 1-dephospho-lipid A obtained from ion-exchange chromatography and a small amount of phospholipid were loaded onto the equilibrated resin. Here, the concentration of the mixture was set to be 0.5 mg/mL or less. Then, the resin was washed with only 5 CV of 100% Buffer A so that the impurities derived from *E. coli* were suffiently wiped off for elution. Here, 4 acyl 1-dephospho-lipid A was eluted together. Then, the resin was washed with only 3 CV of 95% Buffer A to remove the remaining impurities. Here, a small amount of 5 acyl 1-dephospho-lipid A was eluted together. By flowing 10 CV of more of 50% Buffer A, remaining 5 acyl 1-dephospho-lipid A and 6 acyl 1-dephospho-lipid A were eluted by elution. Then, only samples eluted in 50% Buffer A were pooled in a separatory funnel.

Figure 8A:
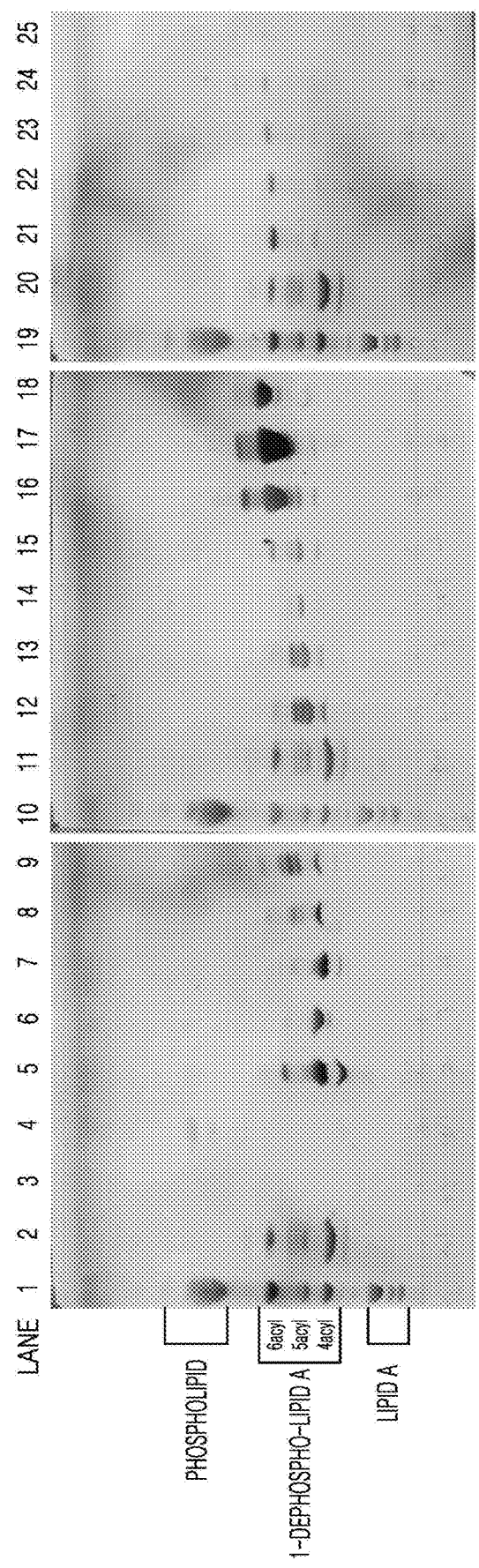
FIG. 8A is an image showing TLC analysis results for each eluate in purification of 1-dephospho-lipid A by reversed-phase chromatography.

The TLC analysis results for each eluate are shown in FIG. 8A [Lanes 1, 10, and 19: total lipids before purification; Lanes 2, 11, and 30:1-dephospho lipid A (load samples) purified by using macro-prep DEAE; Lane 3: flow through; Lanes 4 to 8: 100% Buffer A, 5 CV fractions; Lanes 9, 12, and 13: 5% Buffer A, 3 CV fractions; and Lanes 14 to 18 and 21 to 25: 50% Buffer A, 10 CV fractions].

Figure 8B:
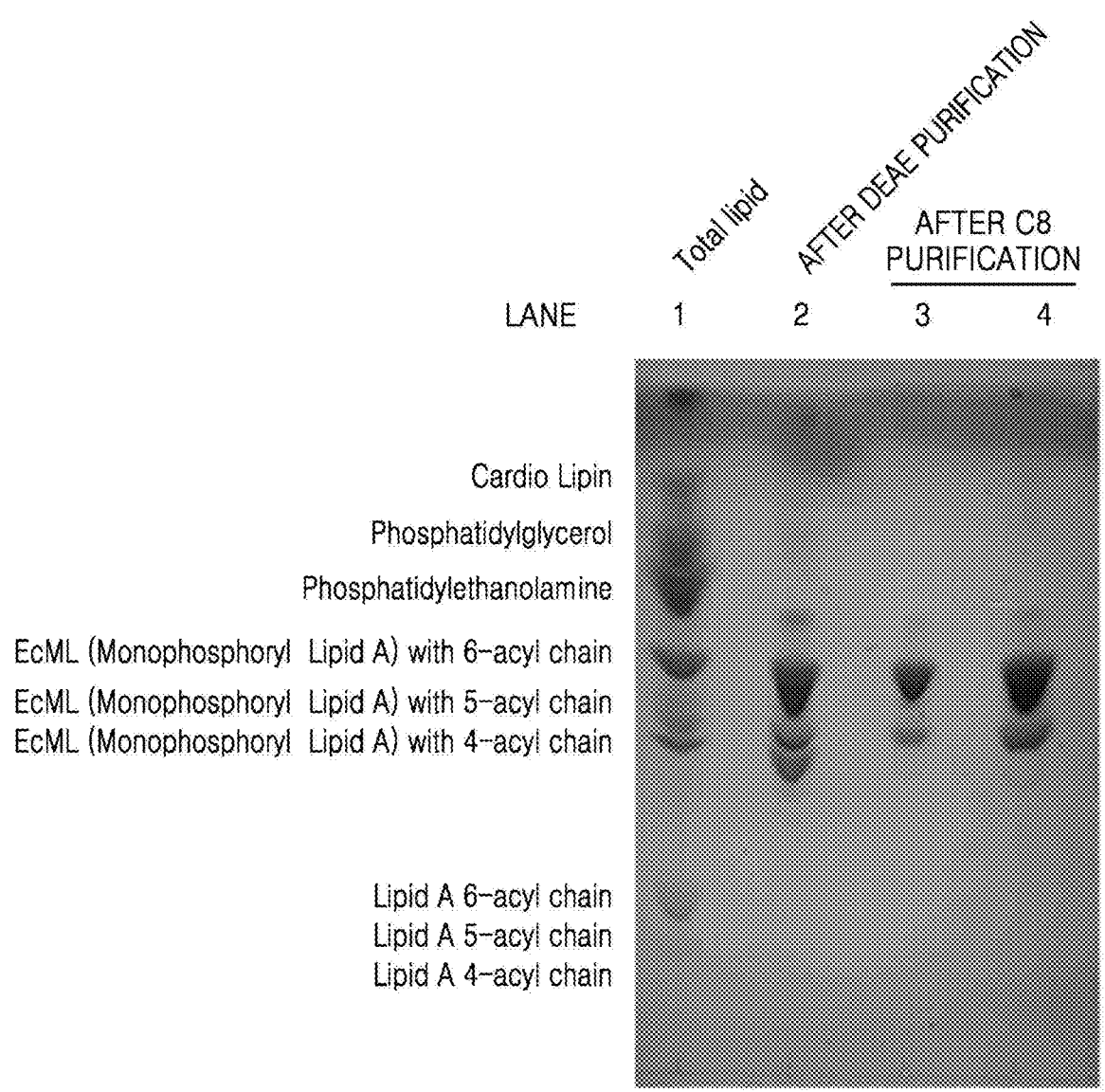
FIG. 8B is an image showing TLC analysis results for each purification step.

In addition, the TLC analysis results for each purification step are shown in FIG. 8B [Lane 1: total lipids before purification; Lane 2:1-dephospho lipid A (load sample) purified by using macro-prep DEAE; Lane 3:1-dephospho lipid A (10 μg) purified under SMT C8 step gradient; and Lane 4:1-dephospho lipid A (20 μg) purified under SMT C8 step gradient].

As shown in FIGS. 8A and 8B, 1-dephospho-lipid A including about 70% or more of 6 acyl 1-dephospho-lipid A.

For buffer exchange and to increase the stability of 1-dephospho-lipid A, 10 mL of chloroform per 60 mL of pooled solution was added for neutralization of ammonium acetate and compositions of the acidic environment. Then, a mixed solution containing HCl and distilled water was added so that the HCl concentration of the entire solution was 0.1 N. Here, the final ratio of chloroform:methanol: distilled water ratio was set to be 2:2:1.8 (v/v). The funnel was mixed well to mix all the solutions evenly, and was left until all the solutions are separated into two layer. Here, a phase change occurred from one phase in which the organic solvent layer including 1-dephospho-lipid A dissolved therein and the aqueous solution layer including lipid A dissolved therein to two phases in which the organic solvent layer and the aqueous solution layer were isolated from each other. By isolating the organic solvent layer only, 1-dephospho-lipid A was obtained.

2.1.10. Analysis by HPLC 1-dephospho-lipid A before and after purification was analyzed by reversed-phase HPLC (RP-HPLC).

Here, a detector used herein was a charged aerosol detector, and the chromatography analysis was performed by using C8 reversed-phase column chromatography (XBRIDGE C8® 3.5 μm 4.6×250 mm (Waters)). Samples were dissolved in 2:1 (v/v) chloroform:methanol at a concentration of 1 mg/mL, and filtered through a 0.2 μm PTFE syringe filter. An injection volume was in a range of about 5 μl to about 20 μl. 10% (v/v) of distilled water was added to an organic solvent containing ammonium acetate and 1% (v/v) acetic acid, and analysis was performed by a gradient of a buffer not containing distilled water. A flow rate set herein was 0.8 mL/min.

Figure 9:
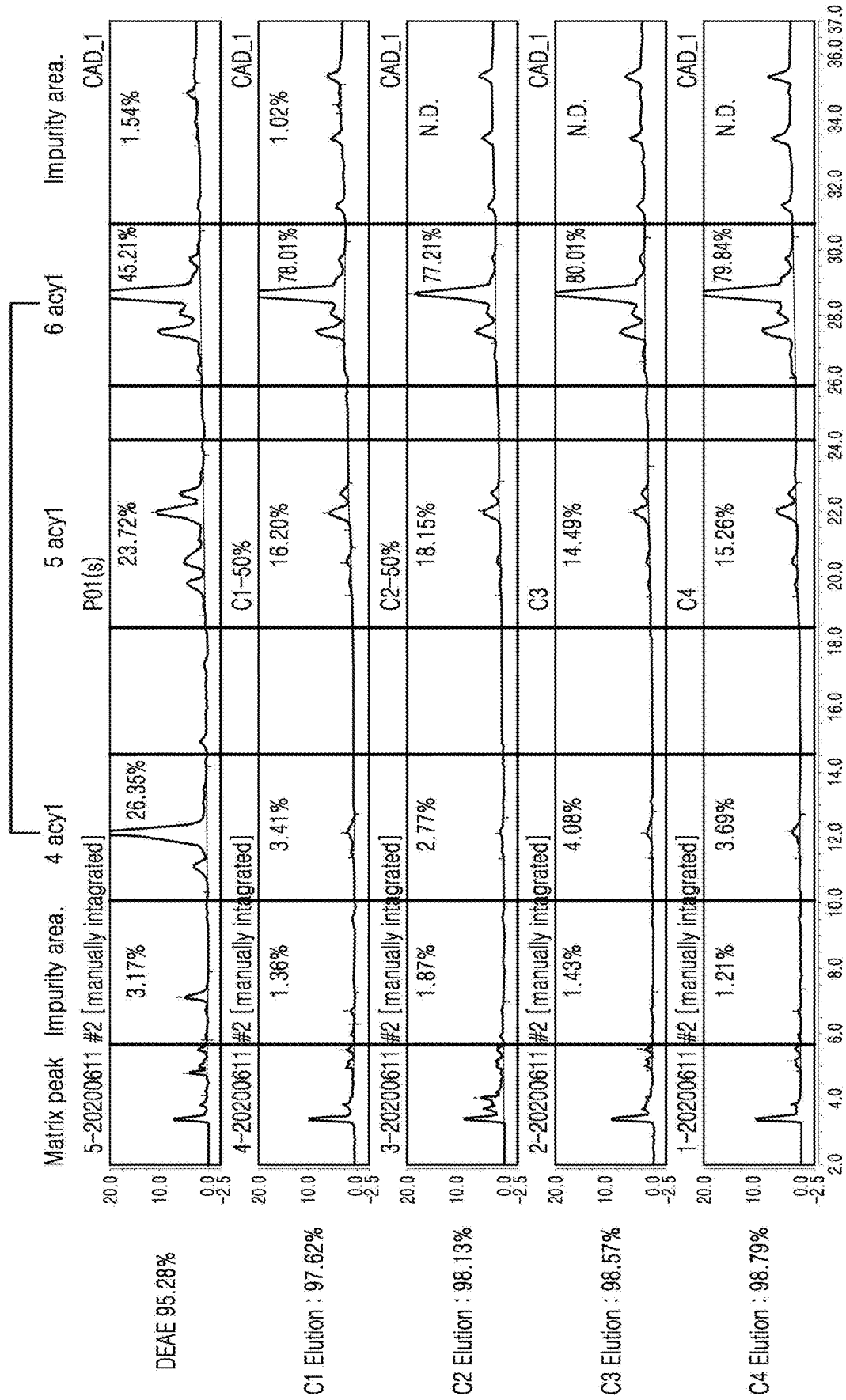
FIG. 9 shows a chromatogram before and after purification of DEAD and C8 by using HPLC.

FIG. 9 shows the results of comparing chromatogram before and after the chromatography purification. Matrix peaks were detected from about 0 minute to about 6 minutes (retention time), and phospholipids, such as phosphatidylethanolamine, phosphatidyl-glycerol, and cardiolipin, were detected as impurities constituting the cell membrane of *E. coli* from about 6 minutes to about 10 minutes. 1-dephospho-lipid A was detected from about 10 minutes to about 15 minutes, 1-dephospho-lipid A of the 5-acyl chain was detected from about 18 minutes to about 24 minutes, and 1-dephospho-lipid A of the 6-acy chain was detected from about 26 minutes to about 30 minutes.

As a result of DEAE purification as shown in FIG. 9, 1-dephospho-lipid A in the 4 acyl, 5 acyl, and 6 acyl chains occupied about 95% (relative area), of which about 45% was 1-dephospho-lipid A of the 6-acyl chain (see the top chromatogram; 1-dephospho-lipid A after DEAE purification).

C8 purification was performed by using the corresponding DEAE elution intermediates, and the chromatogram results are shown in FIG. 9 (see the four chromatograms at the bottom: 1-dephospho-lipid A after C8 purification).

As shown in FIG. 9, the phospholipid impurities and 4 acyl 1-dephospho-lipid A were mostly removed through the C8 purification, and 1-dephospho-lipid A of which the contents of 5 acyl 1-dephospho-lipid A and 6 acyl 1-dephospho-lipid A were in a range of about 97% to about 98% was obtained.

2.1.11. Selective Purification of 1-Dephospho-Lipid A

In reversed-phase chromatography, 6 acyl 1-dephospholipid A was selectively obtained by a linear gradient of Buffer A and Buffer B. Buffer A contains chloroform: methanol:distilled water at a ratio of 15:75:10 (v/v). Buffer B is more polar than Buffer, and contains chloroform: methanol at a ratio of 15:85 (v/v). Both Buffer A and Buffer B contain 5 mM to 20 mM ammonium acetate.

A sample was loaded on a resin with 100% Buffer A, and the resin was washed with 5 CV of Buffer A. Here, phospholipids derived from *E. coli* that can remain after ion-exchange chromatography and 4-acyl 1-dephospho-lipid A were eluted. Afterwards, by the linear gradient from 5% Buffer B to 95% Buffer B, 1-dephospho-lipid A was eluted.

Figure 10A:
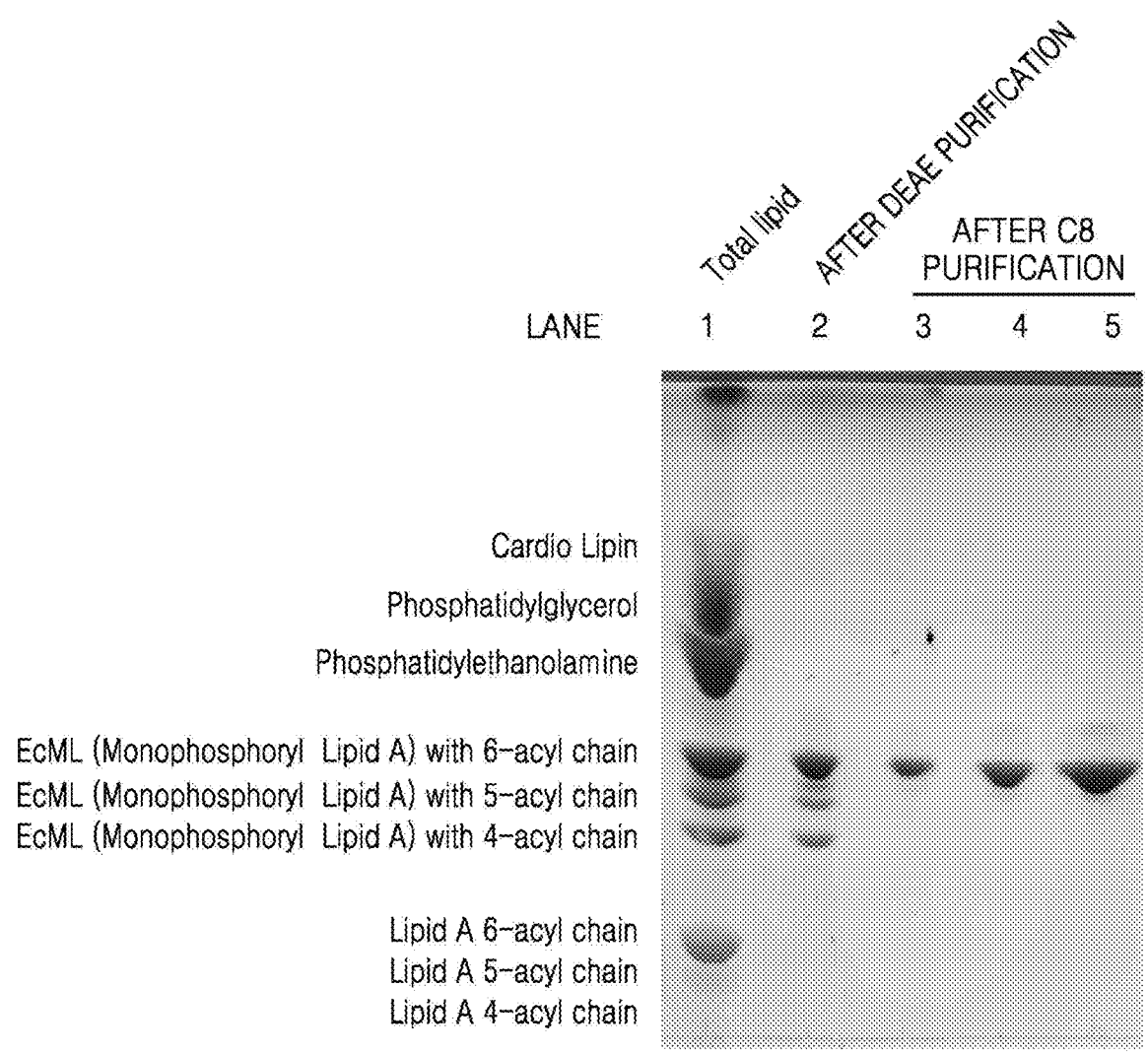
FIG. 10A is an image showing TLC analysis results for 6 acyl 1-dephospho-lipid A after C8 purification by a linear concentration gradient.

The TLC analysis results of 6 acyl 1-dephospho-lipid A after the C8 purification by a linear gradient are shown in FIG. 10A [Lane 1: total lipids before purification; Lane 2:1-dephospho lipid A (load sample) purified by using macro-prep DEAE; Lane 3:1-dephospho lipid A (5 μg) after SMT C8 purification by linear gradient; Lane 4:1-dephospho lipid A (10 μg) after SMT C8 purification by linear gradient; and Lane 5:1-dephospho lipid A (20 μg) after SMT C8 purification by linear gradient].

Figure 10B:
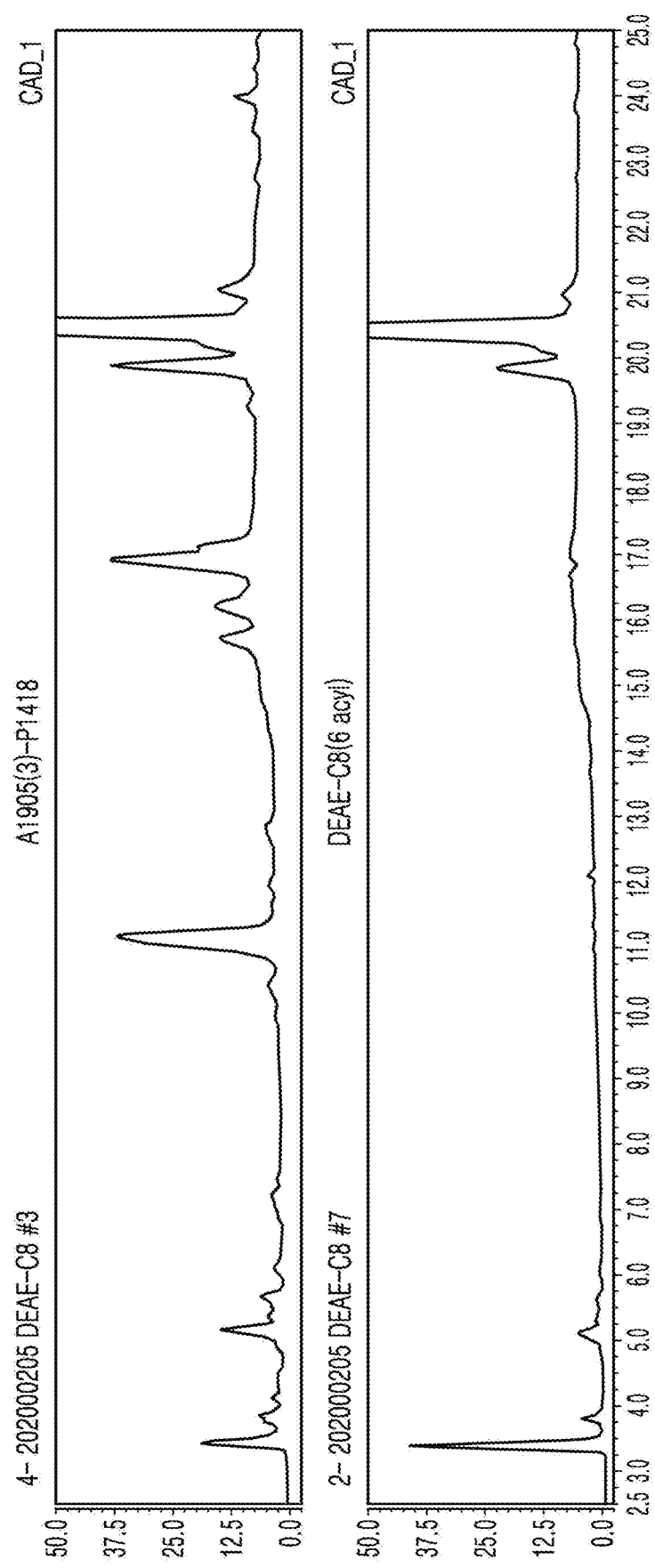
FIG. 10B shows a chromatogram representing selective purification of 1-dephospho-lipid A by using HPLC.

In addition, FIG. 10B shows the chromatogram representing selective purification of 1-dephospho-lipid A by HPLC [upper chromatogram: 1-dephospho-lipid A after DEAE purification, bottom chromatogram: 6 acyl 1-dephospholipid A after selective C8 purification].

Therefore, a process of culturing a genetically modified *E. coli* strain that accumulates 1-dephospho-lipid A in the cell membrane and purifying 1-dephospho lipid A with high purity from the cultured strain was secured.

The invention claimed is:

1. A method of producing monophosphoryl lipid A (MPLA), the method comprising:
   culturing a bacterium producing MPLA, in which the bacterium is cultured from a starting point of an exponential phase until up to 5 hours after a starting point of a stationary phase in a growth curve;
   collecting the bacterium from the culture;
   obtaining lipids from the collected bacterium; and
   isolating MPLA from the obtained lipids;
   wherein the bacterium is a gram-negative bacterium; and
   wherein the isolating MPLA from the obtained lipids includes an anion-exchange chromatography followed by a reverse-phase chromatography;
      wherein the reverse-phase chromatography includes eluting MPLA by a linear gradient of buffer A and buffer B;
         wherein the buffer A is chloroform:methanol:water with 20 mM ammonium acetate (15:75:10, v/v); and
         wherein the buffer B is chloroform:methanol with 20 mM ammonium acetate (15:85, v/v).

2. The method of claim 1, wherein MPLA does not include 2-keto-3-deoxy-D-manno-octulosonate (Kdo).

3. The method of claim 1, wherein the bacterium is cultured until absorbance at a wavelength of 600 nm is in a range of 10 to 70.

4. The method of claim 1, wherein the bacterium is cultured for 10 hours to 30 hours.

5. The method of claim 1, wherein the bacterium is cultured at a temperature in a range of 25° C. to 40° C.

6. The method of claim 1, wherein the bacterium is cultured by batch culture, fed-batch culture, continuous culture, fermentation, or a combination thereof.

7. The method of claim 1, wherein the collecting of the bacterium is performed by centrifugation, filtration, or a combination thereof.

8. The method of claim 1, wherein the obtaining of the lipids is performed by ultrasonication, freeze-thaw cycles, extraction with an organic solvent, or a combination thereof.

9. The method of claim 1, further comprising removing a sugar moiety from the isolated lipids.

10. The method of claim 1, wherein a resin used in the anion-exchange chromatography includes a diethylaminoethyl (DEAE) group, a diethyl-2-hydroxypropylaminoethyl group, a quaternary aminoethyl (QAE) group, or a quaternary ammonium (Q) functional group.

11. The method of claim 1, wherein a buffer used in the anion-exchange chromatography includes ammonium acetate, ammonium formate, pyridinium formate, pyridinium acetate, ammonium carbonate, or a combination thereof.

12. The method of claim 1, wherein an eluent used in the anion-exchange chromatography includes chloroform, methanol, water, or a combination thereof.

13. The method of claim 1, wherein a resin used in the reversed-phase chromatography includes a $C_8$ group, a $C_4$ group, a $C_{18}$ group, a phenyl group, a cyano group, an amine group, or a combination thereof.

14. The method of claim 1, wherein the method produces pentaacyl MLPA and hexaacyl MLPA.

* * * * *

SEQUENCE LISTING

```
<160> NUMBER OF SEQ ID NOS: 25

<210> SEQ ID NO 1
<211> LENGTH: 306
<212> TYPE: PRT
<213> ORGANISM: Artificial
<220> FEATURE:
<223> OTHER INFORMATION: Escherichia coli LpxL polypeptide

<400> SEQUENCE: 1

Met Thr Asn Leu Pro Lys Phe Ser Thr Ala Leu Leu His Pro Arg Tyr
1               5                   10                  15

Trp Leu Thr Trp Leu Gly Ile Gly Val Leu Trp Leu Val Val Gln Leu
            20                  25                  30

Pro Tyr Pro Val Ile Tyr Arg Leu Gly Cys Gly Leu Gly Lys Leu Ala
        35                  40                  45

Leu Arg Phe Met Lys Arg Arg Ala Lys Ile Val His Arg Asn Leu Glu
    50                  55                  60
```

Leu Cys Phe Pro Glu Met Ser Glu Gln Glu Arg Arg Lys Met Val Val
 65                  70                  75                  80

Lys Asn Phe Glu Ser Val Gly Met Gly Leu Met Glu Thr Gly Met Ala
                 85                  90                  95

Trp Phe Trp Pro Asp Arg Arg Ile Ala Arg Trp Thr Glu Val Ile Gly
            100                 105                 110

Met Glu His Ile Arg Asp Val Gln Ala Gln Lys Arg Gly Ile Leu Leu
            115                 120                 125

Val Gly Ile His Phe Leu Thr Leu Glu Leu Gly Ala Arg Gln Phe Gly
            130                 135                 140

Met Gln Glu Pro Gly Ile Gly Val Tyr Arg Pro Asn Asp Asn Pro Leu
145                 150                 155                 160

Ile Asp Trp Leu Gln Thr Trp Gly Arg Leu Arg Ser Asn Lys Ser Met
                165                 170                 175

Leu Asp Arg Lys Asp Leu Lys Gly Met Ile Lys Ala Leu Lys Lys Gly
                180                 185                 190

Glu Val Val Trp Tyr Ala Pro Asp His Asp Tyr Gly Pro Arg Ser Ser
            195                 200                 205

Val Phe Val Pro Leu Phe Ala Val Glu Gln Ala Thr Thr Thr Gly
            210                 215                 220

Thr Trp Met Leu Ala Arg Met Ser Gly Ala Cys Leu Val Pro Phe Val
225                 230                 235                 240

Pro Arg Arg Lys Pro Asp Gly Lys Gly Tyr Gln Leu Ile Met Leu Pro
                245                 250                 255

Pro Glu Cys Ser Pro Pro Leu Asp Asp Ala Glu Thr Thr Ala Ala Trp
                260                 265                 270

Met Asn Lys Val Val Glu Lys Cys Ile Met Met Ala Pro Glu Gln Tyr
                275                 280                 285

Met Trp Leu His Arg Arg Phe Lys Thr Arg Pro Glu Gly Val Pro Ser
290                 295                 300

Arg Tyr
305

<210> SEQ ID NO 2
<211> LENGTH: 921
<212> TYPE: DNA
<213> ORGANISM: Artificial
<220> FEATURE:
<223> OTHER INFORMATION: Polynucleotide encoding Escherichia coli LpxL
      polypeptide

<400> SEQUENCE: 2
atgacgaatc tacccaagtt ctccaccgca ctgcttcatc cgcgttattg gttaacctgg     60
ttgggtattg gcgtactttg gttagtcgtg caattgccct acccggttat ctaccgcctc    120
ggttgtggat taggaaaact ggcgttacgt tttatgaaac gacgcgcaaa aattgtgcat    180
cgcaacctgg aactgtgctt cccggaaatg agcgaacaag aacgccgtaa aatggtggtg    240
aagaatttcg aatccgttgg catgggcctg atggaaaccg gcatggcgtg gttctggccg    300
gaccgccgaa tcgcccgctg gacggaagtg atcggcatgg aacacattcg tgacgtgcag    360
gcgcaaaaac gcggcatcct gttagttggc atccattttc tgacactgga gctgggtgcg    420
cggcagtttg gtatgcagga accgggtatt ggcgtttatc gcccgaacga taatccactg    480
attgactggc tacaaacctg ggccgtttg cgctcaaata atcgatgct cgaccgcaaa    540 gatttaaaag gcatgattaa agccctgaaa aaaggcgaag tggtctggta cgcaccggat    600

```
catgattacg gcccgcgctc aagcgttttc gtcccgttgt ttgccgttga gcaggctgcg    660
accacgaccg gaacctggat gctggcacgg atgtccggcg catgtctggt gcccttcgtt    720
ccacgccgta agccagatgg caaagggtat caattgatta tgctgccgcc agagtgttct    780
ccgccactgg atgatgccga actaccgcc gcgtggatga caaagtggt cgaaaaatgc    840 atcatgatgg caccagagca gtatatgtgg ttacaccgtc gctttaaaac acgcccggaa    900
ggcgttcctt cacgctatta a                                              921
```

<210> SEQ ID NO 3
<211> LENGTH: 48
<212> TYPE: DNA
<213> ORGANISM: Artificial
<220> FEATURE:
<223> OTHER INFORMATION: LpxL forward primer P1

<400> SEQUENCE: 3

```
cgcagtctag aaaggagata tattgatgac gaatctaccc aagttctc                 48
```

<210> SEQ ID NO 4
<211> LENGTH: 67
<212> TYPE: DNA
<213> ORGANISM: Artificial
<220> FEATURE:
<223> OTHER INFORMATION: LpxL reverse primer P2

<400> SEQUENCE: 4

```
cgctattatt tttttcgtt tccattggta tatctccttc ttattaatag cgtgaaggaa    60
cgccttc                                                              67
```

<210> SEQ ID NO 5
<211> LENGTH: 190
<212> TYPE: PRT
<213> ORGANISM: Artificial
<220> FEATURE:
<223> OTHER INFORMATION: Escherichia coli LpxM polypeptide

<400> SEQUENCE: 5

Met Lys Lys Phe Leu Phe Lys Gln Lys Phe Cys Glu Ser Leu Pro Lys
1               5                   10                  15

Ser Phe Ser Lys Thr Leu Leu Ala Leu Ser Leu Gly Leu Ile Leu Leu
            20                  25                  30

Gly Ile Phe Ala Pro Phe Pro Lys Val Pro Lys Gln Pro Ser Val Pro
        35                  40                  45

Leu Met Phe His Phe Thr Glu His Tyr Ala Arg Phe Ile Pro Thr Ile
    50                  55                  60

Leu Ser Val Ala Ile Pro Leu Ile Gln Arg Asp Ala Val Gly Leu Phe
65                  70                  75                  80

Gln Val Ala Asn Ala Ser Ile Ala Thr Thr Leu Leu Thr His Thr Thr
                85                  90                  95

Lys Arg Ala Leu Asn His Val Thr Ile Asn Asp Gln Arg Leu Gly Glu
            100                 105                 110

Arg Pro Tyr Gly Gly Asn Phe Asn Met Pro Ser Gly His Ser Ser Met
        115                 120                 125

Val Gly Leu Ala Val Ala Phe Leu Met Arg Arg Tyr Ser Phe Lys Lys
    130                 135                 140

Tyr Phe Trp Leu Leu Pro Leu Val Pro Leu Thr Met Leu Ala Arg Ile
145                 150                 155                 160

Tyr Leu Asp Met His Thr Ile Gly Ala Val Leu Thr Gly Leu Gly Val
          165                 170                 175

Gly Met Leu Cys Val Ser Leu Phe Thr Ser Pro Lys Lys Pro
        180                 185                 190

<210> SEQ ID NO 6
<211> LENGTH: 972
<212> TYPE: DNA
<213> ORGANISM: Artificial
<220> FEATURE:
<223> OTHER INFORMATION: Polynucleotide encoding Escherichia coli LpxM
      polypeptide

<400> SEQUENCE: 6
atggaaacga aaaaaaataa tagcgaatac attcctgagt ttgataaatc ctttcgccac      60
ccgcgctact ggggagcatg gctgggcgta gcagcgatgg cgggtatcgc tttaacgccg     120
ccaaagttcc gtgatcccat tctggcacgg ctgggacgtt tgccggacg actgggaaaa      180
agctcacgcc gtcgtgcgtt aatcaatctg tcgctctgct ttccagaacg tagtgaagct     240
gaacgcgaag cgattgttga tgagatgttt gccaccgcgc cgcaagcgat ggcaatgatg     300
gctgagttgg caatacgcgg gccggagaaa attcagccgc gcgttgactg caagggctg     360
gagatcatcg aagagatgcg gcgtaataac gagaaagtta tctttctggt gccgcacggt     420
tgggccgtcg atattcctgc catgctgatg gcctcgcaag ggcagaaaat ggcagcgatg     480
ttccataatc agggcaaccc ggttttgat tatgtctgga cacggtgcg tcgtcgcttt      540
ggcggtcgtc tgcatgcgag aaatgacggt attaaaccat tcatccagtc ggtacgtcag     600
gggtactggg gatattattt acccgatcag gatcatggcc cagagcacag cgaatttgtg     660
gatttctttg ccacctataa agcgacgttg cccgcgattg gtcgtttgat gaaagtgtgc     720
cgtgcgcgcg ttgtaccgct gtttccgatt tatgatggca agacgcatcg tctgacgatt     780
caggtgcgcc caccgatgga tgatctgtta gaggcggatg atcatacgat gcgcggcgg     840
atgaatgaag aagtcgagat ttttgttggt ccgcgaccag aacaatacac ctggatacta     900
aaattgctga aaactcgcaa accgggcgaa atccagccgt ataagcgcaa agatctttat     960
cccatcaaat aa                                                        972

<210> SEQ ID NO 7
<211> LENGTH: 67
<212> TYPE: DNA
<213> ORGANISM: Artificial
<220> FEATURE:
<223> OTHER INFORMATION: LpxM forward primer P3

<400> SEQUENCE: 7
gaaggcgttc cttcacgcta ttaataagaa ggagatatac caatggaaac gaaaaaaaat     60
aatagcg                                                              67

<210> SEQ ID NO 8
<211> LENGTH: 37
<212> TYPE: DNA
<213> ORGANISM: Artificial
<220> FEATURE:
<223> OTHER INFORMATION: LpxM reverse primer P3

<400> SEQUENCE: 8
gcagaagctt ttatttgatg ggataaagat ctttgcg                              37

<210> SEQ ID NO 9

```
<211> LENGTH: 29
<212> TYPE: DNA
<213> ORGANISM: Artificial
<220> FEATURE:
<223> OTHER INFORMATION: PL promoter nucleotide sequence

<400> SEQUENCE: 9
ttgacataaa taccactggc ggtgatact                                    29

<210> SEQ ID NO 10
<211> LENGTH: 77
<212> TYPE: DNA
<213> ORGANISM: Artificial
<220> FEATURE:
<223> OTHER INFORMATION: Forward primer amplifying PL promoter

<400> SEQUENCE: 10
ggcagtgagc gcaacgcaga attcttgaca taaataccac tggcggtgat actttcacac   60
aggaaacagc tatgacc                                                 77

<210> SEQ ID NO 11
<211> LENGTH: 77
<212> TYPE: DNA
<213> ORGANISM: Artificial
<220> FEATURE:
<223> OTHER INFORMATION: Reverse primer amplifying PL promoter

<400> SEQUENCE: 11
ggtcatagct gtttcctgtg tgaaagtatc accgccagtg gtatttatgt caagaattct   60
gcgttgcgct cactgcc                                                 77

<210> SEQ ID NO 12

<400> SEQUENCE: 12

000

<210> SEQ ID NO 13
<211> LENGTH: 573
<212> TYPE: DNA
<213> ORGANISM: Artificial
<220> FEATURE:
<223> OTHER INFORMATION: Polynucleodide encoding Helicobactor pylori
      LpxE mutant

<400> SEQUENCE: 13
atgaaaaaat tcttatttaa acaaaaattt tgtgaaagcc tgcccaaatc gtttctaaaa    60
actttgttag cgctcagttt gggcttgatt ttattaggca tttttgcgcc tttccctaaa   120
gtccctaaac agcctagcgt gccttaatg tttcatttca ccgagcatta tgcgcgcttt   180
atccctacga ttttatctgt ggcgattccc ttaatccaaa gagatgcggt agggcttttt   240
caagtcgcta acgcttctat cgctacaacc cttctcacgc acaccaccaa aagagcctta   300
aaccatgtaa caatcaacga tcagcgtttg ggcgagcgcc ttatggagg taatttcaac   360 atgccaagcg ggcattcgtc tatggtgggt ttggcggtgg cgttttaat gcgccgctat   420 tcttttaaaa aatactttg gctcttgccc ctagtccctt tgaccatgct cgctcgcatt   480
tatttagaca tgcacaccat ggcgcggtg ctgaccgggc ttggcgttgg aatgttgtgc   540
gtaagccttt ttacaagccc caaaaagcct taa                                573

<210> SEQ ID NO 14
<211> LENGTH: 55
```

```
<212> TYPE: DNA
<213> ORGANISM: Artificial
<220> FEATURE:
<223> OTHER INFORMATION: Forward primer for amplifying HpLpxE mutant

<400> SEQUENCE: 14
gatcctctag aaaggagata tattgatgaa aaaattctta tttaaacaaa aattt          55

<210> SEQ ID NO 15
<211> LENGTH: 29
<212> TYPE: DNA
<213> ORGANISM: Artificial
<220> FEATURE:
<223> OTHER INFORMATION: Reverse primer for amplifying Helicobactor
      pylori LpxE mutant

<400> SEQUENCE: 15
agctacaagc ttttaaggct ttttggggc                                       29

<210> SEQ ID NO 16
<211> LENGTH: 30
<212> TYPE: DNA
<213> ORGANISM: Artificial
<220> FEATURE:
<223> OTHER INFORMATION: Forward primer for amplifying frt-kan-frt

<400> SEQUENCE: 16
gcagaagctt gtgtaggctg gagctgcttc                                      30

<210> SEQ ID NO 17
<211> LENGTH: 34
<212> TYPE: DNA
<213> ORGANISM: Artificial
<220> FEATURE:
<223> OTHER INFORMATION: Reverse primer for amplifying frt-kan-frt

<400> SEQUENCE: 17
gcagaagctt atgaatatcc tccttagttc ctat                                 34

<210> SEQ ID NO 18
<211> LENGTH: 237
<212> TYPE: PRT
<213> ORGANISM: Artificial
<220> FEATURE:
<223> OTHER INFORMATION: Escherichia coli LpxT polypeptide

<400> SEQUENCE: 18

Met Ile Lys Asn Leu Pro Gln Ile Val Leu Leu Asn Ile Val Gly Leu
1               5                   10                  15

Ala Leu Phe Leu Ser Trp Tyr Ile Pro Val Asn His Gly Phe Trp Leu
            20                  25                  30

Pro Ile Asp Ala Asp Ile Phe Tyr Phe Phe Asn Gln Lys Leu Val Glu
        35                  40                  45

Ser Lys Ala Phe Leu Trp Leu Val Ala Leu Thr Asn Asn Arg Ala Phe
    50                  55                  60

Asp Gly Cys Ser Leu Leu Ala Met Gly Met Leu Met Leu Ser Phe Trp
65                  70                  75                  80

Leu Lys Glu Asn Ala Pro Gly Arg Arg Arg Ile Val Ile Ile Gly Leu
                85                  90                  95

Val Met Leu Leu Thr Ala Val Val Leu Asn Gln Leu Gly Gln Ala Leu
            100                 105                 110

Ile Pro Val Lys Arg Ala Ser Pro Thr Leu Thr Phe Thr Asp Ile Asn
        115                 120                 125
```

```
Arg Val Ser Glu Leu Leu Ser Val Pro Thr Lys Asp Ala Ser Arg Asp
        130                 135                 140

Ser Phe Pro Gly Asp His Gly Met Met Leu Leu Ile Phe Ser Ala Phe
145                 150                 155                 160

Met Trp Arg Tyr Phe Gly Lys Val Ala Gly Leu Ile Ala Leu Ile Ile
                165                 170                 175

Phe Val Val Phe Ala Phe Pro Arg Val Met Ile Gly Ala His Trp Phe
            180                 185                 190

Thr Asp Ile Ile Val Gly Ser Met Thr Val Ile Leu Ile Gly Leu Pro
        195                 200                 205

Trp Val Leu Leu Thr Pro Leu Ser Asp Arg Leu Ile Thr Phe Phe Asp
        210                 215                 220

Lys Ser Leu Pro Gly Lys Asn Lys His Phe Gln Asn Lys
225                 230                 235

<210> SEQ ID NO 19
<211> LENGTH: 714
<212> TYPE: DNA
<213> ORGANISM: Artificial
<220> FEATURE:
<223> OTHER INFORMATION: Polynucleotide encoding Escherichia coli LpxT
      polypeptide

<400> SEQUENCE: 19
atgattaaaa aatttgccgca aatagtgttg ttgaatattg tcggcctcgc gctgtttctt      60
tcctggtata tccccgttaa tcatggattc tggttgccga ttgatgcgga tatttttat      120 ttctttaatc agaaactggt cgaaagtaag gccttttgt ggctggttgc attgaccaac      180
aatcgcgcct tcgacggttg ttcactgctg gcgatgggta tgttgatgct gagtttctgg      240
ctgaaagaaa acgcccctgg cagacgacgt atcgtgatta ttggtctggt catgctatta      300
actgcagtgg tattaaacca gctgggtcag gcattaattc ctgtaaaacg gccagccca      360 acattgactt ttaccgatat taaccgcgtc agcgaactgc tctctgttcc cacgaaagat      420
gcctcacgag atagctttcc cggcgatcac ggcatgatgc tgcttatttt ttcggcattc      480
atgtggcgtt atttcggcaa agttgcaggc cttatcgccc ttattatttt tgtggttttt      540
gcatttccca gagtaatgat tggcgcacac tggtttactg acatcattgt cggttcgatg      600
accgtgatat tgatcggttt gccctgggtg ttgctgacgc cattaagtga tcgattaatc      660 acctttttg acaaatcact accaggaaaa aacaaacatt tccaaaacaa ataa      714

<210> SEQ ID NO 20
<211> LENGTH: 89
<212> TYPE: DNA
<213> ORGANISM: Artificial
<220> FEATURE:
<223> OTHER INFORMATION: Forward primer amplifying bacA::HpLpxE-frt-kan-
      frt

<400> SEQUENCE: 20
aacctggtca tacgcagtag ttcggacaag cggtacattt taataattta ggggtttatt      60
gatgaaaaaa ttcttattta aacaaaaat                                         89

<210> SEQ ID NO 21
<211> LENGTH: 89
<212> TYPE: DNA
<213> ORGANISM: Artificial
<220> FEATURE:
<223> OTHER INFORMATION: Reverse primer amplifying bacA::HpLpxE-frt-kan-
```

-continued frt

<400> SEQUENCE: 21
tgacaacgcc aagcatccga cactattcct caattaaaag aacacgacat acaccgcagc    60
cgccacatga atatcctcct tagttccta                                      89

<210> SEQ ID NO 22
<211> LENGTH: 425
<212> TYPE: PRT
<213> ORGANISM: Artificial
<220> FEATURE:
<223> OTHER INFORMATION: Escherichia coli KdtA polypeptide

<400> SEQUENCE: 22

```
Met Leu Glu Leu Leu Tyr Thr Ala Leu Leu Tyr Leu Ile Gln Pro Leu
1               5                   10                  15

Ile Trp Ile Arg Leu Trp Val Arg Gly Arg Lys Ala Pro Ala Tyr Arg
            20                  25                  30

Lys Arg Trp Gly Glu Arg Tyr Gly Phe Tyr Arg His Pro Leu Lys Pro
        35                  40                  45

Gly Gly Ile Met Leu His Ser Val Ser Val Gly Glu Thr Leu Ala Ala
    50                  55                  60

Ile Pro Leu Val Arg Ala Leu Arg His Arg Tyr Pro Asp Leu Pro Ile
65                  70                  75                  80

Thr Val Thr Thr Met Thr Pro Thr Gly Ser Glu Arg Val Gln Ser Ala
                85                  90                  95

Phe Gly Lys Asp Val Gln His Val Tyr Leu Pro Tyr Asp Leu Pro Asp
            100                 105                 110

Ala Leu Asn Arg Phe Leu Asn Lys Val Asp Pro Lys Leu Val Leu Ile
        115                 120                 125

Met Glu Thr Glu Leu Trp Pro Asn Leu Ile Ala Ala Leu His Lys Arg
    130                 135                 140

Lys Ile Pro Leu Val Ile Ala Asn Ala Arg Leu Ser Ala Arg Ser Ala
145                 150                 155                 160

Ala Gly Tyr Ala Lys Leu Gly Lys Phe Val Arg Arg Leu Leu Arg Arg
                165                 170                 175

Ile Thr Leu Ile Ala Ala Gln Asn Glu Glu Asp Gly Ala Arg Phe Val
            180                 185                 190

Ala Leu Gly Ala Lys Asn Asn Gln Val Thr Val Thr Gly Ser Leu Lys
        195                 200                 205

Phe Asp Ile Ser Val Thr Pro Gln Leu Ala Ala Lys Ala Val Thr Leu
    210                 215                 220

Arg Arg Gln Trp Ala Pro His Arg Pro Val Trp Ile Ala Thr Ser Thr
225                 230                 235                 240

His Glu Gly Glu Glu Ser Val Val Ile Ala Ala His Gln Ala Leu Leu
                245                 250                 255

Gln Gln Phe Pro Asn Leu Leu Leu Ile Leu Val Pro Arg His Pro Glu
            260                 265                 270

Arg Phe Pro Asp Ala Ile Asn Leu Val Arg Gln Ala Gly Leu Ser Tyr
        275                 280                 285

Ile Thr Arg Ser Ser Gly Glu Val Pro Ser Thr Ser Thr Gln Val Val
    290                 295                 300

Val Gly Asp Thr Met Gly Glu Leu Met Leu Leu Tyr Gly Ile Ala Asp
305                 310                 315                 320

Leu Ala Phe Val Gly Gly Ser Leu Val Glu Arg Gly Gly His Asn Pro
```

```
                    325                 330                 335
Leu Glu Ala Ala Ala His Ala Ile Pro Val Leu Met Gly Pro His Thr
                340                 345                 350

Phe Asn Phe Lys Asp Ile Cys Ala Arg Leu Glu Gln Ala Ser Gly Leu
            355                 360                 365

Ile Thr Val Thr Asp Ala Thr Thr Leu Ala Lys Glu Val Ser Ser Leu
        370                 375                 380

Leu Thr Asp Ala Asp Tyr Arg Ser Phe Tyr Gly Arg His Ala Val Glu
385                 390                 395                 400

Val Leu Tyr Gln Asn Gln Gly Ala Leu Gln Arg Leu Leu Gln Leu Leu
                405                 410                 415

Glu Pro Tyr Leu Pro Pro Lys Thr His
                420                 425

<210> SEQ ID NO 23
<211> LENGTH: 1278
<212> TYPE: DNA
<213> ORGANISM: Artificial
<220> FEATURE:
<223> OTHER INFORMATION: Polynucleotide encoding Escherichia coli KdtA
      polypeptide

<400> SEQUENCE: 23
atgctcgaat tgctttacac cgcccttctc taccttattc agccgctgat ctggatacgg      60
ctctgggtgc gcggacgtaa ggctccggcc tatcgaaaac gctggggtga acgttacggt     120
ttttaccgcc atccgctaaa accaggcggc attatgctgc actccgtctc cgtcggtgaa     180
actctggcgg caatcccgtt ggtgcgcgcg ctgcgtcatc gttatcctga tttaccgatt     240
accgtaacaa ccatgacgcc aaccggttcg gagcgcgtac aatcggcttt cgggaaggat     300
gttcagcacg tttatctgcc gtatgatctg cccgatgcac tcaaccgttt cctgaataaa     360
gtcgacccta aactggtgtt gattatggaa accgaactat ggcctaacct gattgcggcg     420
ctacataaac gtaaaattcc gctggtgatc gctaacgcgc gactctctgc ccgctcggcc     480
gcaggttatg ccaaactggg taaattcgtc cgtcgcttgc tgcgtcgtat tacgctgatt     540
gctgcgcaaa atgaagaaga tggtgcacgt tttgtgcgcg tgggcgcaaa aaataatcag     600
gtgaccgtta ccggtagcct gaaattcgat atttctgtaa cgccgcagtt ggctgctaaa     660
gccgtgacgc tgcgccgcca gtgggcacca caccgcccgg tatggattgc caccagcact     720
cacgaaggcg aagagagtgt ggtgatcgcc gcacatcagg cattgttaca gcaattcccg     780
aatttattgc tcatcctggt accccgtcat ccggaacgct tcccggatgc gattaacctt     840
gtccgccagg ctggactaag ctatatcaca cgctcttcag gggaagtccc ctccaccagc     900
acgcaggttg tggttggcga tacgatgggc gagttgatgt tactgtatgg cattgccgat     960
ctcgcctttg ttggcggttc actggttgaa cgtggtgggc ataatccgct ggaagctgcc    1020
gcacacgcta ttccggtatt gatggggccg catactttta actttaaaga catttgcgcg    1080
cggctggagc aggcaagcgg gctgattacc gttaccgatg ccactacgct tgcaaaagag    1140
gtttcctctt tactcaccga cgccgattac cgtagtttct atggccgtca tgccgttgaa    1200
gtactgtatc aaaaccaggg cgcgctacag cgtctgcttc aactgctgga accttacctg    1260
ccaccgaaaa cgcattga                                                  1278

<210> SEQ ID NO 24
<211> LENGTH: 80
<212> TYPE: DNA
```

-continued

```
<213> ORGANISM: Artificial
<220> FEATURE:
<223> OTHER INFORMATION: Forward primer amplifying kdtA::frt-kan-frt

<400> SEQUENCE: 24
gctaaataca tagaatcccc agcacatcca taagtcagct atttactatg ctcgaattgc    60
gtgtaggctg gagctgcttc                                                80

<210> SEQ ID NO 25
<211> LENGTH: 86
<212> TYPE: DNA
<213> ORGANISM: Artificial
<220> FEATURE:
<223> OTHER INFORMATION: Reverse primer amplifying kdtA::frt-kan-frt

<400> SEQUENCE: 25
atcgatatga ccattggtaa tgggatcgaa agtacccgga taaatcgccc gtttttgcat    60
tgaatatcct ccttagttcc tattcc                                         86
```